US012799340B2

(12) United States Patent
Kushiki et al.

(10) Patent No.: US 12,799,340 B2
(45) Date of Patent: Nov. 17, 2026

(54) CALCIUM PHOSPHATE POWDER

(71) Applicant: TOMITA PHARMACEUTICAL CO., LTD., Naruto (JP)

(72) Inventors: Yohei Kushiki, Naruto (JP); Akihito Bando, Naruto (JP); Nozomu Hashimoto, Naruto (JP); Naoyuki Kitamura, Naruto (JP)

(73) Assignee: TOMITA PHARMACEUTICAL CO., LTD., Naruto (JP)

( * ) Notice: Subject to any disclaimer, the term of this patent is extended or adjusted under 35 U.S.C. 154(b) by 878 days.

(21) Appl. No.: 18/007,149

(22) PCT Filed: Jul. 16, 2021

(86) PCT No.: PCT/JP2021/026806
§ 371 (c)(1),
(2) Date: Jan. 27, 2023

(87) PCT Pub. No.: WO2022/024817
PCT Pub. Date: Feb. 3, 2022

(65) Prior Publication Data

US 2023/0227672 A1 Jul. 20, 2023

(30) Foreign Application Priority Data

Jul. 30, 2020 (JP) ................................ 2020-129675

(51) Int. Cl.
*C09D 7/61* (2018.01)
*A61F 2/30* (2006.01)
(Continued)

(52) U.S. Cl.
CPC ................ *C09D 7/61* (2018.01); *A61L 27/12* (2013.01); *A61L 27/56* (2013.01); *B33Y 70/00* (2014.12);
(Continued)

(58) Field of Classification Search
CPC ........................................................ C09D 7/61
See application file for complete search history.

(56) References Cited

U.S. PATENT DOCUMENTS 5,158,756 A † 10/1992 Ogawa
6,283,997 B1 9/2001 Garg et al.
(Continued)

FOREIGN PATENT DOCUMENTS

CN 102153059 A 8/2011
CN 108295306 A 7/2018
(Continued)

OTHER PUBLICATIONS

Huang et al., "Synthesis and characterization of mesoporous hydroxyapatite powder by microemulsion technique", 2019, J Mater Res Tech, 8(3), pp. 3158-3166. (Year: 2019).*
(Continued)

*Primary Examiner* — Robert A Vetere
(74) *Attorney, Agent, or Firm* — Knobbe, Martens, Olson & Bear, LLP

(57) ABSTRACT

An object of the present invention is to provide a calcium phosphate powder that enables the preparation of a slurry for additive manufacturing with excellent dispersion stability, and enables the production of a three-dimensional additive manufacturing article with high strength, in additive manufacturing. Provided is a calcium phosphate powder, having an average particle size ($D_{50}$) of 0.1 to 5.0 μm, and having a pore volume of mesopores (pore size: 2 to 50 nm) of 0.01 to 0.06 cc/g as measured by a gas adsorption method. The calcium phosphate powder has excellent dispersion stability in a slurry for additive manufacturing, and, by performing additive manufacturing using a slurry for additive manufacturing containing the calcium phosphate, it is possible to produce a three-dimensional additive manufacturing article
(Continued)

XRD of Calcium Phosphate Powder of Example 6 with high strength, which is useful as an implant, such as an artificial bone.

5 Claims, 4 Drawing Sheets

(51) Int. Cl.

| | |
|---|---|
| ***A61L 27/12*** | (2006.01) |
| ***A61L 27/56*** | (2006.01) |
| ***B33Y 70/00*** | (2020.01) |
| ***B33Y 80/00*** | (2015.01) |
| ***C01B 25/32*** | (2006.01) |
| ***C09D 4/06*** | (2006.01) |
| ***C09D 7/40*** | (2018.01) |
| ***C09D 133/04*** | (2006.01) |

(52) U.S. Cl.

CPC .............. *B33Y 80/00* (2014.12); *C01B 25/32* (2013.01); *C09D 4/06* (2013.01); *C09D 7/68* (2018.01); *C09D 7/69* (2018.01); *C09D 133/04* (2013.01); *A61F 2002/30962* (2013.01); *A61F 2002/30971* (2013.01); *A61L 2430/02* (2013.01); *C01P 2004/61* (2013.01); *C01P 2004/62* (2013.01); *C01P 2006/12* (2013.01); *C01P 2006/14* (2013.01); *C01P 2006/16* (2013.01)

(56) References Cited

U.S. PATENT DOCUMENTS

| | | | | |
|---|---|---|---|---|
| 2005/0226904 | A1* | 10/2005 | Choi | A61L 27/18 424/443 |
| 2014/0239527 | A1* | 8/2014 | Lee | B29C 64/106 264/17 |
| 2015/0259247 | A1 | 9/2015 | Watanabe | |
| 2017/0360534 | A1* | 12/2017 | Sun | C08L 75/04 |
| 2018/0000571 | A1 | 1/2018 | Watanabe | |
| 2019/0216616 | A1* | 7/2019 | Yang | A61F 2/4601 |
| 2022/0356070 | A1* | 11/2022 | Ishikawa | C01B 25/32 |
| 2023/0227672 | A1 | 7/2023 | Kushiki et al. | |

FOREIGN PATENT DOCUMENTS

| | | | | |
|---|---|---|---|---|
| CN | 110272273 | A | 9/2019 | |
| CN | 110668807 | A | 1/2020 | |
| EP | 2796110 | B1 * | 6/2017 | G09B 23/30 |
| JP | H07-002505 | A | 1/1995 | |
| JP | H09-020508 | A | 1/1997 | |
| JP | 2002-274822 | A | 9/2002 | |
| JP | 2008-184359 | A | 8/2008 | |
| JP | 2015-174792 | A | 10/2015 | |
| JP | 2019-069866 | A | 5/2019 | |
| JP | 7015444 | B1 | 2/2022 | |
| WO | WO 2013/108597 | A1 | 7/2013 | |
| WO | WO 2016/147681 | A1 | 9/2016 | |
| WO | WO 2020212131 | A1 † | 10/2020 | |

OTHER PUBLICATIONS

Huang et al., "Synthesis and characterization of mesoporous hydroxyapatite powder by microemulsion technique," 2019, J. Mater. Res. Technol. 8(3), pp. 3158-3166. (Year: 2019).*

Extended European Search Report for EP Appl. No. 21850836.4 dated Sep. 3, 2024 (in 12 pages).

International Search Report in PCT/JP2021/026806 dated Sep. 7, 2021.

Huang, A. et al., "Synthesis and characterization of mesoporous hydroxyapatite powder by microemulsion technique", *Journal of Materials Research and Technology*, 2019, vol. 8, pp. 3158-3166.

Liu, Z. et al., "Additive manufacturing of hydroxyapatite bone scaffolds via digital light processing and in vitro compatibility", *Ceramics International*, 2019, vol. 45, issue 81, pp. 11079-11086.

Yamazawa, K. et al., "Proposal for Artificial Bone Formation Using Powder-layered Manufacturing: Porous Characteristics of Forming Bone", *Transactions of Japanese Society for Medical and Biological Engineering*; 47(2): 142-147, 2009.

Japanese Office Action App. No. 2022-000297 dated Jul. 1, 2025 (in 4 pages).

Chinese Office Action for Application No. 202180060335.0, dated Dec. 13, 2024 (in 2 pages).

European Office Action for App. No. 21850836.4, dated Jan. 19, 2026 (in 10 pages).

Scalera, F. et al. "Development and characterization of UV curable epoxy/hydroxyapatite suspensions for stereolithography applied to bone tissue engineering", Ceramics International, vol. 40, No. 10, pp. 15455-15462 (2014).

An Huang, et al, Synthesis and characterization of mesoporous Hydroxyapatite powder by microemulsion technique, Journal of Materials Research and Technology, May 23, 2019, pp. 3158-3166, vol. 8, No. 3, DOI: https://doi.org/10.1016/j.jmrt.2019.02.025, Elsevier B.V. (hereinafter "Huang").†

Daniele Ongari, et al, Accurate Characterization of the Pore Volume in Microporous Crystalline Materials, Langmuir, Jun. 21, 2017, pp. 14529-14538, vol. 33, DOI: 10.1021/acs.langmuir.7b01682, American Chemical Society (hereinafter "Ongari").†

Microtrac MRB, Website: Mesopore and Macropore Analysis Calculation Methods explained, Google Index Date Mar. 5, 2009, 2 pages, https://www.microtrac.com/applications/knowledge-base/mesopore-macropore-analysis/ (hereinafter "Microtrao").†

* cited by examiner
† cited by third party

XRD of Calcium Phosphate Powder of Example 6

XRD of Calcium Phosphate Powder of Example 7

XRD of Calcium Phosphate Powder of Example 8

XRD of Calcium Phosphate Powder of Example 9

XRD of Three-Dimensional Additive Manufacturing Article Obtained Using Calcium Phosphate Powder of Example 6

XRD of Three-Dimensional Additive Manufacturing Article Obtained Using Calcium Phosphate Powder of Example 8

CALCIUM PHOSPHATE POWDER

TECHNICAL FIELD

The present invention relates to a calcium phosphate powder that enables the preparation of a slurry for additive manufacturing with excellent dispersion stability, and enables the production of a three-dimensional additive manufacturing article with high strength, in additive manufacturing.

BACKGROUND ART

In recent years, for the treatment of bone diseases, such as bone fractures, artificial bones have been used as an alternative material to human bone for bone defects. Metals, ceramics, polymer materials, and the like are used as materials of artificial bones.

While ceramics are inferior to metals and polymer materials in mechanical strength, they have excellent biocompatibility, and are highly useful as materials of artificial bones. Among ceramics, calcium phosphates such as hydroxyapatite (HAP) and β-tricalcium phosphate (β-TCP) have a composition similar to that of human bone, and have excellent osteoinductive properties. Thus, these calcium phosphates bind directly to bones, or serve as a bone-formation component. Therefore, many studies have been made on artificial bones formed of calcium phosphates.

Unfortunately, although artificial bones formed of calcium phosphates have a composition similar to that of bone, they do not provide a treatment speed as fast as that with autologous bone. Thus, artificial bones formed of calcium phosphates have been developed in granular shapes or block shapes that are porous or have through holes to achieve a structure similar to that of autologous bone. However, these artificial bones have yet to provide a treatment speed as fast as that with autologous bone, and additionally, need to be shaped to conform to defect sites at the time of surgery.

To solve these issues, in the formation of artificial bones using calcium phosphates, attempts have been made not only to shape artificial bones to conform to defect sites using additive manufacturing technologies (3D printers), but also create artificial bones that even reproduce the internal structure of bone. Known 3D printers that are applied to artificial bones include those using a manufacturing process in which a curing liquid is injected to cure a powder (powder-layered manufacturing process); a manufacturing process in which a slurry for additive manufacturing (manufacturing paste) formed by kneading a ceramic raw material with a photo-curable resin is cured by ultraviolet irradiation, and the resin is removed from the resulting cured product (stereolithography process); and the like.

Non Patent Literature 1 discloses that artificial bones were produced by the powder-layered manufacturing process, using a powder containing α-tricalcium phosphate, tetracalcium phosphate, dibasic calcium phosphate, and HAP. However, the resulting artificial bones have a compressive strength of only about 27 MPa. Non Patent Literature 2 discloses that artificial bones were produced by the stereolithography process, using HAP with a particle size of 12 μm. However, the resulting artificial bones have a compressive strength of only about 15 MPa. As discussed above, artificial bones in the prior art produced by additive manufacturing technologies using calcium phosphates have the drawback that they have low compressive strength, and cannot be applied to sites subjected to a high load (such as femur). Patent Literature 1 considers alumina, zirconia, and the like as ceramic raw materials to be used in an additive manufacturing technology. Unfortunately, although these raw materials provide three-dimensional additive manufacturing articles with a certain strength, they have poor osteoinductive properties.

Furthermore, artificial bones produced are required to have bone reproducibility (manufacturing accuracy) to a degree such that they do not need to be shaped during surgery. While it is effective to reduce the particle size of a calcium phosphate powder in an attempt to improve the manufacturing accuracy in the stereolithography process, if the average particle size of the calcium phosphate powder is reduced to 1 μm or less, there is a tendency for the calcium phosphate powder to easily agglomerate in a slurry and cannot be uniformly dispersed.

In view of the above-described prior art as the background, there is a desire for the development of a calcium phosphate powder that enables the preparation of a slurry for additive manufacturing with excellent dispersion stability, and enables the production of a three-dimensional additive manufacturing article with high strength using an additive manufacturing technology.

CITATION LIST

Non Patent Literature

Non Patent Literature 1: Proposal for Artificial Bone Formation Using Powder-layered Manufacturing: Porous Characteristics of Forming Bone. Transactions of Japanese Society for Medical and Biological Engineering; 47(2): 142-147, 2009 Non Patent Literature 2: Additive manufacturing of hydroxyapatite bone scaffolds via digital light processing and in vitro compatibility (Ceramics International Volume 45, Issue 81 June 2019 Pages 11079-11086)

PATENT LITERATURE

Patent Literature 1: WO 2016/147681

SUMMARY OF INVENTION

Technical Problem

It is an object of the present invention to provide a calcium phosphate powder that enables the preparation of a slurry for additive manufacturing with excellent dispersion stability, and enables the production of a three-dimensional additive manufacturing article with high strength, in additive manufacturing.

Solution to Problem

The present inventors have conducted extensive research to solve the aforementioned problem, and found that a calcium phosphate powder, having an average particle size ($D_{50}$) of 0.1 to 5.0 μm, and having a pore volume of mesopores (pore size: 2 to 50 nm) of 0.01 to 0.06 cc/g as measured by a gas adsorption method, has excellent dispersion stability in a slurry for additive manufacturing, and that, by performing additive manufacturing using a slurry for additive manufacturing containing the calcium phosphate, it is possible to produce a three-dimensional additive manufacturing article with high strength, which is useful as an implant, such as an artificial bone. The present invention has been completed by conducting further research based on this finding.

In summary, the present invention provides aspects of the invention as listed below.

Item 1. A calcium phosphate powder, having an average particle size ($D_{50}$) of 0.1 to 5.0 μm, and having a pore volume of mesopores (pore size: 2 to 50 nm) of 0.01 to 0.06 cc/g as measured by a gas adsorption method.

Item 2. The calcium phosphate powder according to item 1, wherein the calcium phosphate contains at least one of hydroxyapatite, tricalcium phosphate, α-TCP, calcium-deficient hydroxyapatite, and β-TCP.

Item 3. The calcium phosphate powder according to item 1 or 2, wherein the calcium phosphate powder has a BET specific surface area of 0.1 to 20 $m^2/g$.

Item 4. The calcium phosphate powder according to any one of items 1 to 3, wherein the calcium phosphate powder has a pore volume of macropores (pore size: 50 to 200 nm) of 0.02 to 0.10 cc/g as measured by the gas adsorption method.

Item 5. The calcium phosphate powder according to any one of items 1 to 4, wherein the calcium phosphate powder has a $D_{10}$ of 3.0 μm or less as measured using a laser diffraction/scattering particle size distribution analyzer.

Item 6. The calcium phosphate powder according to any one of items 1 to 5, wherein the $D_{10}$ is 1.0 μm or less.

Item 7. A material for additive manufacturing comprising the calcium phosphate powder according to any one of items 1 to 6.

Item 8. The material for additive manufacturing according to item 7, which is used for stereolithography.

Item 9. The material for additive manufacturing according to item 7 or 8, which is used for production of an implant.

Item 10. A slurry for additive manufacturing comprising the calcium phosphate powder according to any one of items 1 to 6 and a photocurable resin.

Item 11. A method for producing a three-dimensional additive manufacturing article, comprising the following steps (1) to (4):

(1) forming a slurry layer using the slurry for additive manufacturing according to item 10;

(2) curing the slurry layer by irradiation of laser light in a predetermined pattern shape;

(3) repeating steps (1) and (2) to form a three-dimensional layered cured product; and (4) removing uncured resin and cured resin from the three-dimensional layered cured product.

Item 12. The method for producing a three-dimensional additive manufacturing article according to item 11, wherein the three-dimensional additive manufacturing article is an implant.

Item 13. Use of the calcium phosphate powder according to any one of items 1 to 6 as a material for additive manufacturing.

Advantageous Effects of Invention

The calcium phosphate powder of the present invention enables the preparation of a slurry for additive manufacturing with excellent dispersion stability. Furthermore, a three-dimensional additive manufacturing article produced using the slurry for additive manufacturing containing the calcium phosphate powder of the present invention can have high strength, and is useful as an artificial bone for use at a load-bearing site, such as femur.

DESCRIPTION OF EMBODIMENTS

Figure 1:
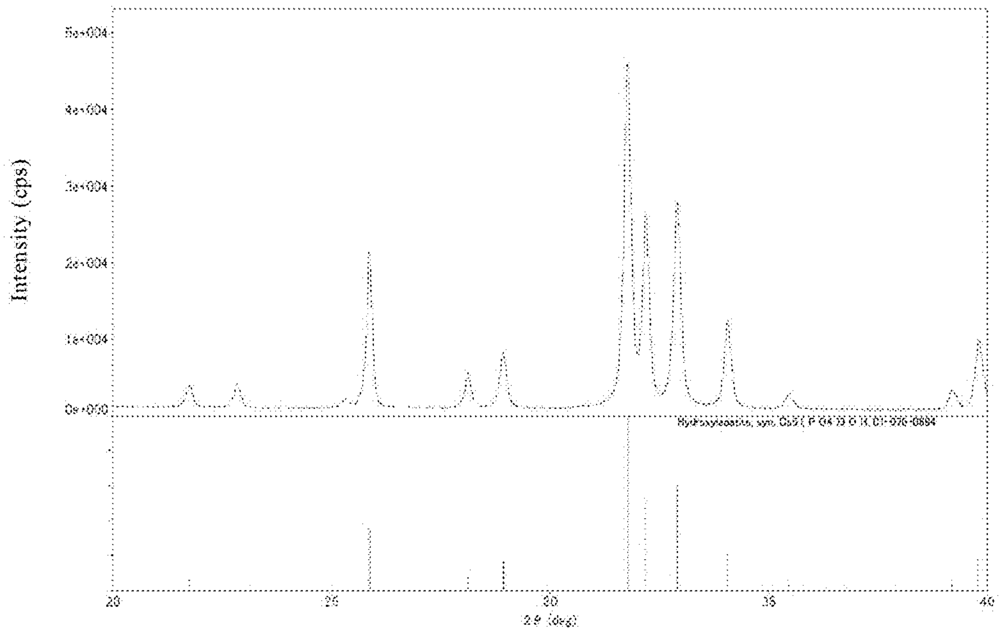
FIG. 1 shows the result of measuring the crystal structure for the calcium phosphate powder of Example 6.

A calcium phosphate powder of the present invention has an average particle size ($D_{50}$) of 0.1 to 5.0 μm, and has a pore volume of mesopores (pore size: 2 to 50 nm) of 0.01 to 0.06 cc/g as measured by a gas adsorption method. The calcium phosphate powder of the present invention will be hereinafter described in detail.

[Type of Calcium Phosphate]

The calcium phosphate powder of the present invention may be any of the following types: hydroxyapatite (HAP: ($Ca_5(PO_4)_3(OH)$)), β-TCP (β-$Ca_3(PO_4)_2$), calcium-deficient hydroxyapatite ($Ca_{10-z}(HPO_4)_z(PO_4)_{6-z}(OH)_{2-z}$ (where $0<Z\leq1$), α-tricalcium phosphate (α-$Ca_3(PO_4)_2$), tricalcium phosphate ($Ca_3(PO_4)_2$), and octacalcium phosphate ($Ca_8(PO_4)_4(HPO_4)_2(OH)_2$); or may be a mixture or a mixed crystal containing two or more of them. The calcium-deficient hydroxyapatite may be either anhydrous or hydrated, and the structural formula of hydrated calcium-deficient hydroxyapatite is, for example, $Ca_{10-z}(HPO_4)_z(PO_4)_{6-z}(OH)_{2-z}\cdot nH_2O$ (where $0<Z\leq1$ and $0<n\leq2.5$).

Among the calcium phosphates, HAP and β-TCP have excellent biocompatibility, and are useful as materials of artificial bones. Thus, suitable examples of the calcium phosphate powder of the present invention include HAP powder, β-TCP powder, calcium-deficient hydroxyapatite powder, and a mixed powder or a mixed crystal powder thereof. One example of the mixed powder or the mixed crystal powder is a mixed powder or a mixed crystal powder of β-TCP and calcium-deficient hydroxyapatite. While the ratio of β-TCP and calcium-deficient hydroxyapatite contained in the mixed powder or the mixed crystal powder of β-TCP and calcium-deficient hydroxyapatite is not limited, the ratio may be such that the β-TCP content is 2 to 98% by weight and the calcium-deficient hydroxyapatite content is 2 to 98% by weight, and preferably, the β-TCP content is 30 to 98% by weight and the calcium-deficient hydroxyapatite content is 2 to 70% by weight, as measured according to the RIR (Reference Intensity Ratio) method in X-ray diffraction measurement.

The calcium phosphate powder of the present invention may be either a sintered body that has been subjected to sintering treatment or a non-sintered body that has not been subjected to sintering treatment. When the calcium phosphate powder is a HAP powder, it is preferably a non-sintered body, from the viewpoint of favorably imparting the predetermined range of the average particle size ($D_{50}$) and the predetermined range of the pore volume of mesopores (pore size: 2 to 50 nm) to the calcium phosphate powder.

[Physical Properties of Calcium Phosphate Powder]

The calcium phosphate powder of the present invention has an average particle size ($D_{50}$) of 0.1 to 5.0 μm. When the pore volume of mesopores (pore size: 2 to 50 nm) is set to the predetermined value and simultaneously, the average particle size is in this range, the calcium phosphate powder of the present invention can have excellent dispersion stability in a slurry for additive manufacturing and simultaneously, can impart high strength to the resulting three-dimensional additive manufacturing article. From the viewpoint of further improving the dispersion stability in a slurry for additive manufacturing and the strength of the resulting three-dimensional additive manufacturing article, the average particle size ($D_{50}$) of the calcium phosphate powder of the present invention is preferably 0.1 to 3.0 μm, and more preferably 0.4 to 1.0 μm, for example. Alternatively, the average particle size ($D_{50}$) of the calcium phosphate powder of the present invention is preferably 0.5 to 5.0 μm, more preferably 1.0 to 5.0 μm, and still more preferably 3.0 to 5.0 μm. As used herein, the "average particle size ($D_{50}$)" of the calcium phosphate powder refers to the particle size (median size) when the cumulative percentage reaches 50% in a volume-based cumulative particle size distribution as measured using a laser diffraction/scattering particle size distribution analyzer.

While the $D_{10}$ of the calcium phosphate powder of the present invention is not limited as long as the average particle size ($D_{50}$) is in the above-defined range, the $D_{10}$ is, for example, 3.0 μm or less or 1 μm or less. The $D_{10}$ of the calcium phosphate powder of the present invention is preferably 0.1 to 2.5 μm, more preferably 0.1 to 0.9 μm, and still more preferably 0.2 to 0.8 μm. When the $D_{10}$ of the calcium phosphate powder of the present invention is in this range, the pore volume per particle increases, which can further improve the dispersion stability in a slurry for additive manufacturing. As used herein, the "$D_{10}$" of the calcium phosphate powder refers to the particle size when the cumulative percentage reaches 10% in a volume-based cumulative particle size distribution as measured using a laser diffraction/scattering particle size distribution analyzer.

While the $D_{90}$ of the calcium phosphate powder of the present invention is not limited as long as the average particle size ($D_{50}$) is in the above-defined range, the $D_{90}$ is, for example, 1 to 30 μm, preferably 1 to 20 μm, and more preferably 2 to 18 μm. As used herein, the "$D_{90}$" of the calcium phosphate powder refers to the particle size when the cumulative percentage reaches 90% in a volume-based cumulative particle size distribution as measured using a laser diffraction/scattering particle size distribution analyzer.

While the number average diameter of the calcium phosphate powder of the present invention is not limited as long as the average particle size ($D_{50}$) is in the above-defined range, the number average diameter is, for example, 0.1 to 3 μm, preferably 0.1 to 2 μm, more preferably 0.1 to 1 μm, and still more preferably 0.1 to 0.6 μm. As used herein, the "number average diameter" of the calcium phosphate powder refers to the particle size when the cumulative percentage calculated in terms of number reaches 50% in a number-based cumulative particle size distribution as measured using a laser diffraction/scattering particle size distribution analyzer.

The pore volume of mesopores (pore size: 2 to 50 nm) of the calcium phosphate powder of the present invention as measured by a gas adsorption method is 0.01 to 0.06 cc/g. When the average particle size ($D_{50}$) is in the above-defined range and simultaneously, the pore volume of mesopores (pore size: 2 to 50 nm) is in this range, the calcium phosphate powder of the present invention can have excellent dispersion stability in a slurry for additive manufacturing, such that the resin and the particles do not separate from each other in the slurry for additive manufacturing, and molecules in the resin can be bound by hydrogen bonding or the like, and the calcium phosphate powder of the present invention can have thixotropic properties required for forming a layer during additive manufacturing, in which the hydrogen bonding or the like is separated when a force is applied during additive manufacturing, and the viscosity decreases. Furthermore, when the pore volume of mesopores (pore size: 2 to 50 nm) is in the above-defined range, irregularities of the particles on the surface of the three-dimensional additive manufacturing article can be reduced, which allows the production of a three-dimensional additive manufacturing article with high accuracy. Conversely, if the pore volume of mesopores (pore size: 2 to 50 nm) is less than 0.01 cc/g, the dispersion stability of the slurry for additive manufacturing decreases, resulting in a tendency for dilatancy to occur in which the particles are brought close to one another when a force is applied during additive manufacturing, and the viscosity increases. From the viewpoint of further improving the dispersion stability in a slurry for additive manufacturing and the strength of the resulting three-dimensional additive manufacturing article, the pore volume of mesopores (pore size: 2 to 50 nm) of the calcium phosphate powder of the present invention is preferably 0.02 to 0.06 cc/g, and more preferably 0.02 to 0.05 cc/g.

As used herein, the "pore volume of mesopores (pore size: 2 to 50 nm) as measured by a gas adsorption method" of the calcium phosphate powder is the value as measured according to the following method, using a high-speed specific surface area and pore distribution analyzer. First, 0.1 g or 1.0 g of the calcium phosphate powder is accurately weighed and sealed in a sorbent tube, and then degassed at 105° C. for 3 hours. Then, a nitrogen gas adsorption isotherm under a liquid nitrogen gas temperature is obtained, and the pore volume (cc/g) of mesopores (2 to 50 nm) is calculated using the BJH method.

While the pore volume of macropores (50 to 200 nm) of the calcium phosphate powder of the present invention as measured by the gas adsorption method is not limited, it is, for example, 0.02 to 0.10 cc/g, preferably 0.02 to 0.09 cc/g, and more preferably 0.02 to 0.08 cc/g. When the pore volume of macropores is in this range, the dispersion stability in a slurry for additive manufacturing can be further improved. As used herein, the "pore volume of macropores (50 to 200 nm) as measured by the gas adsorption method" of the calcium phosphate powder is the value as measured according to the following method, using a high-speed specific surface area and pore distribution analyzer. First, 0.1 g or 1.0 g of the calcium phosphate powder is accurately weighed and sealed in a sorbent tube, and then degassed at 105° C. for 3 hours. Then, a nitrogen gas adsorption isotherm under a liquid nitrogen gas temperature is obtained, and the pore volume (cc/g) of macropores (50 to 200 nm) is calculated using the BJH method.

While the BET specific surface area of the calcium phosphate powder of the present invention is not limited, it is, for example, 20 $m^2/g$ or less, preferably 0.1 to 20 $m^2/g$, more preferably 5 to 20 $m^2/g$, and still more preferably 8 to 18 $m^2/g$. When the BET specific surface area is in this range, the particles can tightly shrink during degreasing and/or sintering of the resulting three-dimensional additive manufacturing article, which allows the creation of a three-dimensional additive manufacturing article with an even higher strength. As used herein, the "BET specific surface area" of the calcium phosphate powder is the value as measured according to the following method, using a high-speed specific surface area and pore distribution analyzer. First, 0.1 g or 1.0 g of the calcium phosphate is accurately weighed and sealed in a sorbent tube, and then degassed at 105° C. for 3 hours. Then, a nitrogen gas adsorption isotherm under a liquid nitrogen gas temperature is obtained, and the specific surface area ($m^2/g$) is calculated according to the multi-point BET method, using the adsorption isotherm.

While the average pore size of the calcium phosphate powder of the present invention as measured by the gas adsorption method is not limited, it is, for example, 10 to 50 nm, preferably 20 to 40 nm, and more preferably 15 to 35 nm.

As used herein, the "average pore size as measured by the gas adsorption method" of the calcium phosphate powder of the present invention refers to the value obtained using the following method:

First, using a high-speed specific surface area and pore distribution analyzer, the total pore volume is measured using the gas adsorption method, under the following operation conditions:

pretreatment: 0.1 g or 1.0 g of the calcium phosphate powder is accurately weighed and sealed in a sorbent tube, and then degassed at 105° C. for 3 hours.

measurement and analysis: a nitrogen gas adsorption isotherm under a liquid nitrogen gas temperature is obtained, and the total pore volume (cc/g) is calculated from the gas adsorption amount at a relative pressure $P/P_0$ ($P_0$: saturation vapor pressure) of 0.995.

Then, using the BET specific surface area and the total pore volume (gas adsorption method) obtained above, the average pore size is calculated according to the following formula:

average pore size (nm)=4V/S×1000

V: total pore volume (gas adsorption method) (cc/g)

S: BET specific surface area ($m^2/g$)

While the loose bulk density of the calcium phosphate powder to be used in the present invention is not limited, it is, for example, 0.1 to 1.0 g/mL, preferably 0.1 to 0.5 g/mL, and more preferably 0.1 to 0.3 g/mL.

As used herein, the "loose bulk density" of the calcium phosphate powder is the value obtained as follows. The calcium phosphate powder is allowed to fall into a cup (capacity: 10 $cm^3$, inner diameter: 2.2 cm, height: 2.6 cm) from a sieve with a mesh size of 710 μm while vibrating the sieve at an amplitude of 0.5 mm. The falling of the calcium phosphate powder is stopped at the point when the cup is filled with the calcium phosphate powder to overflowing. The powder is leveled by removing the portion of the powder raised from the top of the cup, and the weight of the empty cup is subtracted from the weight of the cup containing the powder, and then the powder weight per mL is calculated as the loose bulk density.

While the packed bulk density (tapped density) of the calcium phosphate powder to be used in the present invention is not limited, it is, for example, 0.2 to 1.5 g/mL, preferably 0.3 to 1.0 g/mL, and more preferably 0.4 to 0.8 g/mL.

As used herein, the "packed bulk density" of the calcium phosphate powder is the value obtained as follows. First, the calcium phosphate powder is allowed to fall into a cup (capacity: 10 $cm^3$, inner diameter: 2.2 cm, height: 2.6 cm) from a sieve with a mesh size of 710 μm while vibrating the sieve at an amplitude of 0.5 mm. The falling of the calcium phosphate powder is stopped at the point when the cup is filled with the calcium phosphate powder to overflowing, and the powder is leveled by removing the portion of the powder raised from the top of the cup. Then, a cylinder (inner diameter: 2.2 cm, height: 3.2 cm) is mounted to the top portion of the cup, and the calcium phosphate powder is allowed to fall into the cup from the sieve with a mesh size of 710 μm while vibrating the sieve at an amplitude of 0.5 mm, until the cylinder is filled with the calcium phosphate powder to about 80% of the capacity of the cylinder. Tapping is started in this state, and tapping is performed a total of 180 times. During tapping, when the amount of the calcium phosphate powder in the cylinder is compacted to about 20% of the capacity of the cylinder, the calcium phosphate powder is allowed to fall again into the cylinder through the sieve with a mesh size of 710 μm that is being vibrated at an amplitude of 0.5 mm, until the cylinder is refilled with the calcium phosphate powder to about 80% of the capacity of the cylinder. After the completion of 180 times of tapping, the cylinder is removed, the powder is leveled by removing the portion of the powder raised from the top of the cup, and the weight of the cup containing the powder is measured. From this weight, the weight of the empty cup is subtracted to calculate the powder weight in the cup, and the powder weight per $cm^3$ is obtained as the packed density (g/mL).

[Method for Producing Calcium Phosphate Powder]

The method for producing the calcium phosphate powder of the present invention is not limited as long as it produces a calcium phosphate powder with the above-described physical properties. Suitable examples of the method include the following first method including steps 1-1 to 1-4, the following second method including steps 2-1 to 2-4, and the following third method including steps 3-1 to 3-2.

First Method

Step 1-1: producing calcium phosphate using (1) a wet method in which phosphoric acid and/or a phosphoric acid salt is added dropwise to a suspension in which a calcium salt is suspended such that the molar ratio Ca/P is 1.40 to 1.80, and the mixture is reacted at 30° C. or more, or (2) a wet method in which a suspension in which a calcium salt is suspended is added dropwise to an aqueous phosphoric acid solution in which phosphoric acid and/or a phosphoric acid salt is dissolved in water such that the molar ratio Ca/P is 1.40 to 1.80, and the mixture is reacted at 30° C. or more;

Step 1-2: subjecting the calcium phosphate obtained in step 1-1 to wet grinding to produce a slurry;

Step 1-3: subjecting the slurry obtained in step 1-2 to hydrothermal treatment at 250 to 300° C. to produce a hydrothermally treated product; and Step 1-4: drying the hydrothermally treated product obtained in step 1-3 to produce a calcium phosphate powder.

Second Method

Step 2-1: producing calcium phosphate using a wet method in which a suspension in which a calcium salt is suspended and an aqueous phosphoric acid solution in which phosphoric acid and/or a phosphoric acid salt is dissolved in water are simultaneously added dropwise to an aqueous medium such that the molar ratio Ca/P is 1.40 to 1.80, and the mixture is reacted at 30° C. or more;

Step 2-2: subjecting the calcium phosphate obtained in step 2-1 to wet grinding to produce a slurry;

Step 2-3: subjecting the slurry obtained in step 2-2 to hydrothermal treatment at 150 to 300° C. to produce a hydrothermally treated product; and Step 2-4: drying the hydrothermally treated product obtained in step 2-3 to produce a calcium phosphate powder.

Third Method

Step 3-1: producing calcium phosphate using a wet method in which a suspension at 50° C. or less in which a calcium salt is suspended and an aqueous phosphoric acid solution at 50° C. or less in which phosphoric acid and/or a phosphoric acid salt is dissolved in water are simultaneously added dropwise to an aqueous medium at 80° C. or more such that the molar ratio Ca/P is 1.40 to 1.80, and the mixture is reacted, wherein the reaction is carried out at pH 8.5 to 9.5 or pH 3.5 to 4.5; and Step 3-2: drying the slurry obtained in step 3-1 to produce a calcium phosphate powder.

The first method is specifically described hereinafter.

In step 1-1, the synthesis reaction of calcium phosphate is carried out by reacting calcium ions and phosphate ions, using (1) a wet method in which phosphoric acid and/or a phosphoric acid salt is added dropwise to a suspension in which a calcium salt is suspended such that the molar ratio Ca/P is 1.40 to 1.80, or (2) a wet method in which a suspension in which a calcium salt is suspended is added dropwise to an aqueous phosphoric acid solution in which phosphoric acid and/or a phosphoric acid salt is dissolved in water such that the molar ratio Ca/P is 1.40 to 1.80.

While the calcium salt to be used as a raw material in step 1-1 is not limited in type, examples include inorganic salts and organic acid salts. Specific examples of inorganic salts include calcium chloride, calcium nitrate, calcium carbonate, calcium oxide, and calcium hydroxide. Specific examples of organic acid salts include calcium formate, calcium acetate, calcium lactate, calcium gluconate, and calcium citrate.

While the phosphoric acid salt to be used as a raw material in step 1-1 is not limited in type, examples include alkali metal salts and ammonium salts of phosphoric acid. Examples of alkali metal salts of phosphoric acid include sodium salts and potassium salts, and more specifically, disodium hydrogen phosphate, sodium dihydrogen phosphate, trisodium phosphate, dipotassium hydrogen phosphate, potassium dihydrogen phosphate, tripotassium phosphate, diammonium hydrogen phosphate, ammonium dihydrogen phosphate, and triammonium phosphate.

When producing a HAP powder, it is preferred to use calcium hydroxide as the calcium salt and phosphoric acid as the phosphoric acid and/or phosphoric acid salt, in step 1-1. When producing a β-TCP powder, or a mixed powder or a mixed crystal powder of β-TCP and calcium-deficient hydroxyapatite, it is preferred to use calcium hydroxide or calcium nitrate as the calcium salt and phosphoric acid or diammonium hydrogen phosphate as the phosphoric acid and/or phosphoric acid salt, in step 1-1.

In step 1-1, the dropwise addition rate at which the aqueous solution of the phosphoric acid and/or phosphoric acid salt is added dropwise to the suspension in which the calcium salt is suspended may be adjusted appropriately such that the pH of the reaction mixture after the dropwise addition is adjusted to 9 or less.

For example, when synthesizing HAP by adding the phosphoric acid and/or phosphoric acid salt to the suspension in which the calcium salt is suspended, the dropwise addition rate may be in a range in which the dropwise addition rate of phosphorus (P) atoms is 0.05 to 0.7 mol/h, preferably 0.1 to 0.6 mol/h, and more preferably 0.2 mol/h, per mole of calcium (Ca) atoms. When synthetizing HAP by adding the suspension in which the calcium salt is suspended to the aqueous phosphoric acid solution in which the phosphoric acid and/or phosphoric acid salt is dissolved in water, the dropwise addition rate may be in a range in which the dropwise addition rate of calcium (Ca) atoms is 0.05 to 2.0 mol/h, preferably 0.1 to 1.0 mol/h, and more preferably 0.5 to 0.6 mol/h, per mole of phosphorus (P) atoms.

For example, when synthesizing β-TCP, or a mixed powder or a mixed crystal powder of β-TCP and calcium-deficient hydroxyapatite, by adding the phosphoric acid and/or phosphoric acid salt to the suspension in which the calcium salt is suspended, the dropwise addition rate may be in a range in which the dropwise addition rate of phosphorus (P) atoms is 0.01 to 0.6 mol/h, preferably 0.1 to 0.4 mol/h, and more preferably 0.2 to 0.3 mol/h, per mole of calcium (Ca) atoms. When synthesizing β-TCP by adding the suspension in which the calcium salt is suspended to the aqueous phosphoric acid solution in which the phosphoric acid and/or phosphoric acid salt is dissolved in water, the dropwise addition rate may be in a range in which the dropwise addition rate of calcium (Ca) atoms is 0.05 to 1.8 mol/h, preferably 0.1 to 1.0 mol/h, and more preferably 0.5 to 0.6 mol/h, per mole of phosphorus (P) atoms.

In step 1-1, the dropwise addition amount of the aqueous solution of the phosphoric acid and/or phosphoric acid salt or the dropwise addition amount of the suspension in which the calcium salt is suspended may be set appropriately according to the type of calcium phosphate to be produced, such that the molar ratio Ca/P at the completion of the dropwise addition is in the range of 1.40 to 1.80. For example, when producing a HAP powder, the molar ratio Ca/P at the completion of the dropwise addition is preferably set to 1.0 to 2.5, more preferably 1.5 to 1.8, and still more preferably about 1.67. When producing a β-TCP powder, or a mixed powder or a mixed crystal powder of β-TCP and calcium-deficient hydroxyapatite, the molar ratio Ca/P at the completion of the dropwise addition is preferably set to 0.5 to 2.0, more preferably 1.0 to 1.7, and still more preferably about 1.50.

In step 1-1, the temperature at which the calcium salt and the phosphoric acid and/or phosphoric acid salt are allowed to coexist (reaction temperature) may be set appropriately according to the dropwise addition amount, the dropwise addition rate, and the like; for example, it is 30° C. or more, preferably 40 to 100° C., more preferably 80 to 100° C., and still more preferably 90 to 100° C. To produce a reaction mixture by reacting calcium ions and phosphate ions more efficiently, it is desirable that the whole amount of the calcium salt and the whole amount of the phosphoric acid and/or phosphoric acid salt are allowed to coexist and are then aged at the above-defined temperature condition. As used herein, "aging" refers to allowing to stand still or with stirring for a certain time. While the aging time in step 1-1 may be set appropriately according to the dropwise addition amount, the dropwise addition rate, the reaction temperature, and the like, it is, for example, 10 minutes or more, preferably 10 to 120 minutes, and more preferably 30 to 90 minutes. As used herein, "aging time" refers to the time in which the whole amount of the calcium salt and the whole amount of the phosphoric acid and/or phosphoric acid salt are allowed to stand still or with stirring, starting from 0 minute defined as the point when the whole amount of the calcium salt and the whole amount of the phosphoric acid and/or phosphoric acid salt are allowed to coexist in water. For example, when the aqueous solution of the phosphoric acid and/or phosphoric acid salt is added dropwise to the suspension in which the calcium salt is suspended, "aging time" refers to the time calculated starting from 0 minute defined as the point when the dropwise addition of the aqueous solution of the phosphoric acid and/or phosphoric acid salt is completed.

By performing step 1-1 as described above, a reaction mixture containing the calcium phosphate produced is obtained.

In step 1-2, the calcium phosphate obtained in step 1-1 is subjected to wet grinding to produce a slurry (wet-ground product).

In step 1-2, the reaction mixture after step 1-1 may be subjected to wet grinding as it is. Alternatively, a concentrated solution obtained by concentrating the reaction mixture after step 1-1 may be subjected to wet grinding, or a suspension in which the calcium phosphate recovered from the reaction mixture after step 1-1 by a process such as dehydration and water washing is freshly suspended in an organic solvent such as an alcohol or water may be subjected to wet grinding.

In step 1-2, the method of wet grinding is not limited, and the wet grinding may be performed using any of modes such as impact, shear-type, attrition-type, compression, and vibration. The type of wet grinding apparatus is also not limited, and may be any of apparatuses such as a high-pressure fluid collision mill, a high-speed rotating slit mill, an attritor, a ball mill, a bead mill, a roll mill, a ring-shaped grinding medium mill, and a high-speed spinning thin-film mill. These apparatuses themselves may be known or commercial apparatuses. Among these wet grinding apparatuses, a bead mill can be preferably used.

When a bead mill is used as a wet grinding apparatus, the type of beads is not limited; however, the beads are preferably made of a zirconia-based material. The beads may have a size of, for example, about 0.1 to 3 mm in diameter. While the loading ratio of the beads may be set appropriately according to the size and the like of the apparatus to be used, it may be adjusted appropriately in the range of about 50 to 90% by volume, for example.

While the degree of wet grinding may be adjusted appropriately in step 1-2, the degree of wet grinding is preferably adjusted such that the calcium phosphate powder after the wet grinding has an average particle size of 10 μm or less, preferably 0.1 to 5 μm, and has a maximum particle size of 50 μm or less, preferably 0.1 to 30 μm, from the viewpoint of efficiently producing the calcium phosphate powder of the present invention. As used herein, the "average particle size" and the "maximum particle size" of the calcium phosphate powder after the wet grinding are respectively the "particle size (median size) when the cumulative percentage reaches 50%" and the "maximum particle size" in a volume-based cumulative particle size distribution as measured using a laser diffraction/scattering particle size distribution analyzer.

While the liquid temperature during the wet grinding in step 1-2 is not limited and may be set appropriately according to the heat resistance and the like of the apparatus to be used, it is, for example, about 0 to 100° C., and preferably about 5 to 60° C.

In step 1-3, the slurry obtained in step 1-2 is subjected to hydrothermal treatment (also referred to as hydrothermal synthesis) to produce a hydrothermally treated product. While the solids concentration in the slurry to be subjected to hydrothermal treatment is not limited, it may typically be 1 to 30% by weight, and preferably about 5 to 20% by weight. To adjust the solids concentration in the slurry to be subjected to hydrothermal treatment, the slurry obtained in step 1-2 may be dehydrated and water-washed and then resuspended to give a desired solids concentration.

The hydrothermal treatment in step 1-3 may be performed using a known apparatus such as an autoclave.

While the temperature of the hydrothermal treatment in step 1-3 may be any temperature in the range of 250 to 300° C., it is preferably 260 to 280° C. If the temperature of the hydrothermal treatment in step 1-3 is below 250° C., the resulting calcium phosphate powder does not have the above-described physical properties, and the calcium phosphate powder of the present invention cannot be obtained.

While the time of the hydrothermal treatment in step 1-3 may be a time sufficient for the desired calcium phosphate to be produced, it is typically 1 to 5 hours, and preferably about 1 to 3 hours. As used herein, the "time of the hydrothermal treatment" refers to the time during which the above-defined temperature of the hydrothermal treatment is reached, and does not include the temperature increase time until the above-defined temperature of the hydrothermal treatment is reached and the temperature decrease time after the hydrothermal treatment.

In step 1-4, the hydrothermally treated product obtained in step 1-3 is dried to produce a calcium phosphate powder.

While the mode of drying to be used in step 1-4 is not limited, examples include tray drying, spray drying, box drying, band drying, vacuum drying, freeze drying, microwave drying, a drum dryer, and fluid drying. Among these, tray drying is preferred, for example.

While the drying temperature in step 1-4 is not limited, it is, for example, about 30 to 150° C., and preferably about 80 to 105° C.

The calcium phosphate powder obtained after step 1-4 may be optionally subjected to firing treatment. While the temperature condition for the firing treatment is not limited, it is typically 200 to 1300° C., preferably 200 to 800° C., more preferably 350 to 750° C., and still more preferably 300 to 600° C. The time of the firing treatment may be set appropriately taking into account the firing temperature, in a range in which a calcium phosphate powder with the above-described physical properties can be obtained, and the time of the firing treatment is sufficient if the above-defined temperature condition is reached even momentarily. The holding time of the above-defined temperature condition is preferably 0.1 to 10 hours, and more preferably 1 to 5 hours.

Additionally, after step 1-4 or after the firing treatment, the calcium phosphate powder may be optionally subjected to treatment such as crushing or grinding, for the purpose of adjusting the particle size. It is also desirable that the calcium phosphate powder after step 1-4 or after the firing treatment is subjected to removal of particles with large particle sizes falling outside the above-described physical properties, using a sieve. While the mesh size of the sieve to be used is not limited, it is, for example, 150 μm or less, and preferably 100 to 40 μm.

The second method is specifically described next.

In step 2-1, the synthesis reaction of calcium phosphate is carried out by reacting calcium ions and phosphate ions, using a wet method in which a suspension in which a calcium salt is suspended and an aqueous phosphoric acid solution in which phosphoric acid and/or a phosphoric acid salt is dissolved in water are simultaneously added dropwise to an aqueous medium such that the molar ratio Ca/P is 1.40 to 1.80.

In step 2-1, the type of the calcium salt or the phosphoric acid salt to be used as a raw material, suitable raw materials for producing a HAP powder, suitable raw materials for producing a β-TCP powder, or a mixed powder or a mixed crystal powder of β-TCP and calcium-deficient hydroxyapatite, and the like are the same as in step 1-1 above.

In step 2-1, the aqueous medium to which the raw materials are added dropwise is preferably water.

In step 2-1, the dropwise addition amount of the suspension in which the calcium salt is suspended and the dropwise addition amount of the aqueous phosphoric acid solution in which the phosphoric acid and/or phosphoric acid salt is dissolved in water may be set appropriately according to the type of calcium phosphate to be produced, such that the molar ratio Ca/P at the completion of the dropwise addition is in the range of 1.40 to 1.80. A suitable molar ratio Ca/P when producing a HAP powder, and a suitable molar ratio Ca/P when producing a β-TCP powder, or a mixed powder or a mixed crystal powder of β-TCP and calcium-deficient hydroxyapatite, are the same as in step 1-1 above.

In step 2-1, the dropwise addition rate of the suspension in which the calcium salt is suspended and the dropwise addition rate of the aqueous phosphoric acid solution in which the phosphoric acid and/or phosphoric acid salt is dissolved in water are not limited, and may be adjusted appropriately according to the production scale and the like, such that the pH of the reaction mixture during the dropwise addition is adjusted to 5 to 9, for example. Moreover, in step 2-1, the dropwise addition amount of the aqueous solution of the phosphoric acid and/or phosphoric acid salt and the dropwise addition amount of the suspension in which the calcium salt is suspended may be set appropriately according to the type of calcium phosphate to be produced, such that the molar ratio Ca/P at the completion of the dropwise addition is in the range of 1.40 to 1.80. For example, when producing a HAP powder, the molar ratio Ca/P at the completion of the dropwise addition is preferably set to 1.0 to 2.5, more preferably 1.5 to 1.8, and still more preferably about 1.67. When producing a β-TCP powder, or a mixed powder or a mixed crystal powder of β-TCP and calcium-deficient hydroxyapatite, the molar ratio Ca/P at the completion of the dropwise addition is preferably set to 0.5 to 2.0, more preferably 1.0 to 1.7, and still more preferably about 1.50.

In step 2-1, the temperature at which the calcium salt and the phosphoric acid and/or phosphoric acid salt are allowed to coexist (reaction temperature) is the same as in step 1-1 above.

In step 2-1, it is preferred that aging is performed at a predetermined reaction temperature. The aging time is the same as in step 1-1 above.

In step 2-2, the reaction mixture obtained in step 2-1 is subjected to wet grinding to produce a slurry (wet-ground product). In step 2-2, the method of wet grinding, the degree of wet grinding, the liquid temperature during the wet grinding, and the like are the same as in step 1-2 above.

In step 2-3, the slurry obtained in step 2-2 is subjected to hydrothermal treatment to produce a hydrothermally treated product. In step 2-3, the solids concentration in the slurry to be subjected to hydrothermal treatment, the apparatus for hydrothermal treatment, and the like are the same as in step 1-3 above. While the temperature of the hydrothermal treatment in step 2-3 may be any temperature in the range of 150 to 300° C., it is preferably 200 to 300° C., and more preferably 200 to 280° C. The time of the hydrothermal treatment in step 2-3 is the same as in step 1-3 above.

In step 2-4, the hydrothermally treated product obtained in step 2-3 is dried to produce a calcium phosphate powder.

In step 2-4, the mode of drying, the drying temperature, and the like are the same as in step 1-4 above.

The calcium phosphate powder obtained after step 2-4 may be optionally subjected to firing treatment. The temperature condition for the firing treatment is the same as in the first method above. Additionally, after step 2-4 or after the firing treatment, the calcium phosphate powder may be optionally subjected to treatment such as crushing or grinding, or sieving, for the purpose of adjusting the particle size. For sieving, the mesh size of the sieve to be used is the same as in the first method above.

The third method is specifically described next.

In step 3-1, the synthesis reaction of calcium phosphate is carried out by reacting calcium ions and phosphate ions, using a wet method in which a suspension in which a calcium salt is suspended and an aqueous phosphoric acid solution in which phosphoric acid and/or a phosphoric acid salt is dissolved in water are simultaneously added dropwise to an aqueous medium at 80° C. or more such that the molar ratio Ca/P is 1.40 to 1.80.

In step 3-1, the type of the calcium salt or the phosphoric acid salt to be used as a raw material, suitable raw materials for producing a HAP powder, suitable raw materials for producing a β-TCP powder, or a mixed powder or a mixed crystal powder of β-TCP and calcium-deficient hydroxyapatite, and the like are the same as in step 1-1 above.

In step 3-1, the temperature of the suspension in which the calcium salt is suspended used as a raw material and the temperature of the aqueous phosphoric acid solution in which the phosphoric acid and/or phosphoric acid salt is dissolved in water used as a raw material may both be any temperature in the range of 50° C. or less, and may be preferably set to 40° C. or less, more preferably 30° C. or less, particularly preferably 1 to 30° C.

In step 3-1, the aqueous medium to which the raw materials are added dropwise is preferably water.

In step 3-1, the temperature of the aqueous medium may be any temperature in the range of 80° C. or more, and may be preferably set to 90° C. or more, more preferably 95° C. or more, particularly preferably 95 to 100° C.

In step 3-1, the dropwise addition amount of the suspension in which the calcium salt is suspended and the dropwise addition amount of the aqueous phosphoric acid solution in which the phosphoric acid and/or phosphoric acid salt is dissolved in water may be set appropriately according to the type of calcium phosphate to be produced, such that the molar ratio Ca/P at the completion of the dropwise addition is in the range of 1.40 to 1.80. A suitable molar ratio Ca/P when producing a HAP powder, and a suitable molar ratio Ca/P when producing a β-TCP powder, or a mixed powder or a mixed crystal powder of β-TCP and calcium-deficient hydroxyapatite, are the same as in step 1-1 above.

In step 3-1, the rate at which the suspension in which the calcium salt is suspended and the aqueous phosphoric acid solution in which the phosphoric acid and/or phosphoric acid salt is dissolved in water are simultaneously added dropwise may be set appropriately such that the pH of the reaction mixture during the dropwise addition is adjusted to 8.5 to 9.5 or 3.5 to 4.5. Specifically, when producing a HAP powder, the rate of simultaneous dropwise addition may be set such that the pH of the reaction mixture during the dropwise addition is adjusted to 8.5 to 9.5. When producing a β-TCP powder, or a mixed powder or a mixed crystal powder of β-TCP and calcium-deficient hydroxyapatite, the rate of simultaneous dropwise addition may be set such that the pH of the reaction mixture during the dropwise addition is adjusted to 3.5 to 4.5.

In step 3-1, the dropwise addition amount of the aqueous solution of the phosphoric acid and/or phosphoric acid salt and the simultaneous dropwise addition amount of the suspension in which the calcium salt is suspended may be set appropriately according to the type of calcium phosphate to be produced, such that the molar ratio Ca/P at the completion of the dropwise addition is in the range of 1.40 to 1.80. For example, when producing a HAP powder, the molar ratio Ca/P at the completion of the dropwise addition is preferably set to 1.0 to 2.5, more preferably 1.5 to 1.8, still more preferably about 1.67. When producing a β-TCP powder, or a mixed powder or a mixed crystal powder of β-TCP and calcium-deficient hydroxyapatite, the molar ratio Ca/P at the completion of the dropwise addition is preferably set to 0.5 to 2.0, more preferably 1.0 to 1.7, still more preferably about 1.50.

In step 3-1, the temperature at which the calcium salt and the phosphoric acid and/or phosphoric acid salt are allowed to coexist (reaction temperature) may be any temperature in the range of 80° C. or more, and may be preferably set to 90° C. or more, more preferably 95° C. or more, particularly preferably 95 to 100° C.

In step 3-1, it is preferred that aging is performed at a predetermined reaction temperature. The aging time is the same as in step 1-1 above.

In step 3-2, the reaction mixture obtained in step 3-1 is dried to produce a calcium phosphate powder. In step 3-2, the mode of drying, the drying temperature, and the like are the same as in step 1-4 above.

The calcium phosphate powder obtained after step 3-2 may be optionally subjected to firing treatment. The temperature condition for the firing treatment is the same as in the first method above. Additionally, after step 3-2 or after the firing treatment, the calcium phosphate powder may be optionally subjected to treatment such as wet grinding, crushing or grinding, or sieving, for the purpose of adjusting the particle size. For wet grinding, the method of wet grinding, the degree of wet grinding, the liquid temperature during the wet grinding, and the like are the same as in step 1-2 above. For sieving, the mesh size of the sieve to be used is the same as in the first method above.

[Uses/Material for Additive Manufacturing]

While uses of the calcium phosphate powder of the present invention are not limited, the calcium phosphate powder of the present invention is suitably used as a material for additive manufacturing. As used herein, “material for additive manufacturing” refers to a substance serving as a base material of a three-dimensional additive manufacturing article.

When the calcium phosphate powder of the present invention is used as a material for additive manufacturing, it may be applied to either a stereolithography process or a powder-layered manufacturing process; however, it is suitable as a material for additive manufacturing for stereolithography.

When the calcium phosphate powder of the present invention is to be used as a material for additive manufacturing for stereolithography, a slurry for additive manufacturing (manufacturing paste) containing the calcium phosphate of the present invention and a photocurable resin (ultraviolet curable resin) may be prepared and then subjected to stereolithography.

While the content of the calcium phosphate powder of the present invention in the slurry for additive manufacturing may be in a range in which the slurry for additive manufacturing can exhibit thixotropic properties, it is, for example, 40 to 90% by weight, preferably 60 to 90% by weight, and more preferably 70 to 85% by weight.

While the type of the photocurable resin to be used in the slurry for additive manufacturing is not limited, examples include an acrylic photocurable resin. The content of the photocurable resin in the slurry for additive manufacturing is, for example, 5 to 60% by weight, preferably 5 to 57% by weight, and more preferably 6 to 24% by weight.

The slurry for additive manufacturing may contain a photopolymerization initiator, a dispersing agent (such as a polycarboxylic acid), a thickener, an antioxidant, a light stabilizer, and the like, as long as they do not interfere with the effects of the present invention. When the slurry for additive manufacturing contains a photopolymerization initiator, the content of the photopolymerization initiator is, for example, 0.5 to 15% by weight, and preferably 0.5 to 10% by weight, although not limited thereto. When the slurry for additive manufacturing contains a dispersing agent, the content of the dispersing agent is, for example, 0.1 to 50% by weight, and preferably 8 to 40% by weight, although not limited thereto.

To produce a three-dimensional additive manufacturing article by stereolithography using the slurry for additive manufacturing containing the calcium phosphate powder of the present invention, the following steps (1) to (4) may be performed:

(1) forming a slurry layer using the slurry for additive manufacturing;
(2) curing the slurry layer by irradiation of laser light in a predetermined pattern shape;
(3) repeating steps (1) and (2) to form a three-dimensional layered cured product; and
(4) removing uncured resin and cured resin from the three-dimensional layered cured product.

In step (1), the slurry layer may be adjusted to a thickness of about 5 to 200 μm, for example. The type of laser light to be used in step (2) may be any that can cure the photocurable resin, for example, ultraviolet laser.

In step (4), the uncured resin may be removed by washing with ethanol, for example.

In step (4), the cured resin may be removed by, for example, performing degreasing treatment. As used herein, “degreasing treatment” refers to the treatment for removing the cured resin by heating. The degreasing treatment may use an electric furnace or the like that can perform heating.

While the temperature condition for the degreasing treatment is not limited, it is typically 100 to 600° C., and preferably 300 to 600° C. While the time of the degreasing treatment may be set appropriately in a range in which the cured resin can be removed, it is typically in the range of 1 to 100 hours, preferably 10 to 50 hours, more preferably 10 to 20 hours.

For the purpose of improving the strength of the three-dimensional additive manufacturing article, sintering treatment may be performed after step (4). The apparatus used in the degreasing treatment may be used for the sintering treatment.

While the temperature condition for the sintering treatment is not limited, it is typically 600 to 1500° C., preferably 800 to 1500° C., more preferably 1000 to 1400° C., and particularly preferably 1100 to 1300° C. The time of the sintering treatment may be set appropriately taking into account the degreasing treatment, and is typically 1 to 12 hours, and preferably 1 to 5 hours.

Alternatively, the three-dimensional layered cured product may be subjected to the degreasing treatment and the sintering treatment in a single continuous operation. When the degreasing treatment and the sintering treatment are performed in a single continuous operation, the temperature condition in an electric furnace or the like may be set in a stepwise manner. For example, the temperature condition may be set in a stepwise manner such that, after the above-defined temperature condition for the degreasing treatment and the holding time thereof are maintained, the temperature is increased, and the temperature condition for the sintering treatment and the holding time thereof are maintained. This allows degreasing of the cured resin and sintering of the calcium phosphate powder to be performed in a single continuous operation.

The three-dimensional additive manufacturing article produced using the calcium phosphate powder of the present invention is used, for example, as an artificial joint, a dental implant, an implant such as an artificial bone, and the like. Furthermore, the three-dimensional additive manufacturing article produced using the calcium phosphate powder of the present invention can have high strength and thus, can be suitably used as an artificial bone at a site subjected to a high load, such as femur.

EXAMPLES

The present invention will be more specifically described hereinafter with examples; however, the present invention is not limited thereto.

1. Production and Evaluation of Calcium Phosphate Powders 1-1. Production of Calcium Phosphate Powders

Example 1

1200.0 g of a 20% by weight calcium hydroxide suspension and 742.1 g of a 32% by weight aqueous phosphoric acid solution were prepared such that the molar ratio Ca/P was 1.67. Each of the liquids was preheated to 80° C., and the liquids were simultaneously added dropwise to 1785.0 mL of water heated to 98° C. while stirring at 300 rpm over 1 hour, while controlling the temperature to be maintained at 98° C. and the pH of the reaction mixture to be maintained in the range of 7.0 to 7.5. After the completion of the dropwise addition, the reaction mixture was further aged with stirring for 30 minutes, and then the precipitated crystals of hydroxyapatite were filtered and water-washed.

Subsequently, the resulting product was suspended in water such that the hydroxyapatite content was 10% by weight, and the suspension was subjected to wet grinding using an Ultra Apex Mill (Kotobuki Industries Co., Ltd.; UAM-015) under 41.6 Hz, a pump speed of 2, a zirconia bead diameter of 0.3 mm, and a bead amount of 400 g (loading: 64%). Then, the resulting solution was subjected to hydrothermal treatment in an autoclave (Taiatsu Glass Kogyo K.K.; model TAS-09-20-300) at 200° C. for 3 hours. The resulting product was further subjected to tray drying under a temperature condition of 100° C. using a forced convection constant temperature oven (Yamato Scientific Co., Ltd.; DKM400), and subjected to dry grinding using a micro-pulverizer (Hosokawa Micron Corporation; AP-B) to give calcium phosphate (HAP) particles.

Example 2

1200.0 g of a 20% by weight calcium hydroxide suspension and 742.1 g of a 32% by weight aqueous phosphoric acid solution were prepared such that the molar ratio Ca/P was 1.67. Each of the liquids was preheated to 80° C., and the liquids were simultaneously added dropwise to 1785.0 mL of water heated to 98° C. while stirring at 300 rpm over 1 hour, while controlling the temperature to be maintained at 98° C. and the pH of the reaction mixture to be maintained in the range of 7.0 to 7.5. After the completion of the dropwise addition, the reaction mixture was further aged with stirring for 30 minutes.

Then, the precipitated crystals of hydroxyapatite were subjected to wet grinding using an Ultra Apex Mill (Kotobuki Industries Co., Ltd.; UAM-015) under 41.6 Hz, a pump speed of 2, a zirconia bead diameter of 0.3 mm, and a bead amount of 400 g (loading: 64%). Then, the resulting solution was subjected to hydrothermal treatment in an autoclave (Taiatsu Glass Kogyo K.K.; model TAS-09-20-300) at 280° C. for 3 hours. The resulting product was further subjected to tray drying under a temperature condition of 100° C. using a forced convection constant temperature oven (Yamato Scientific Co., Ltd.; DKM400), and subjected to dry grinding using a micro-pulverizer (Hosokawa Micron Corporation; AP-B) to give calcium phosphate (HAP) particles.

Example 3

3514.1 g of an 8.4 wt % calcium hydroxide suspension and 464.5 g of a 50 wt % aqueous phosphoric acid solution were prepared such that the molar ratio Ca/P was 1.67. The phosphoric acid was added dropwise to the calcium hydroxide suspension heated to 95° C. while stirring at 300 rpm over 3 hours, and then the reaction mixture was further aged with stirring for 1 hour.

Subsequently, the resulting product was subjected to wet grinding using an Ultra Apex Mill (Kotobuki Industries Co., Ltd.; UAM-015) under 41.6 Hz, a pump speed of 2, a zirconia bead diameter of 0.3 mm, and a bead amount of 400 g (loading: 64%). Then, the resulting solution was subjected to hydrothermal treatment in an autoclave (Taiatsu Glass Kogyo K.K.; model TAS-09-20-300) at 280° C. for 3 hours. The resulting product was further subjected to tray drying under a temperature condition of 100° C. using a forced convection constant temperature oven (Yamato Scientific Co., Ltd.; DKM400), and subjected to dry grinding using a micro-pulverizer (Hosokawa Micron Corporation; AP-B) to give calcium phosphate (HAP) particles.

Example 4

The HAP particles obtained in Example 2 were fired at 600° C. for 3 hours (temperature increase rate: 100° C./h) using an electric furnace (Kusaba Chemical Co., Ltd.; KY-5NX) to give calcium phosphate (HAP) particles.

Example 5

Calcium phosphate (HAP) particles were obtained under the same conditions as in Example 4, except that the firing temperature was changed to 300° C.

Example 6

92.5 kg of a 20% by weight calcium hydroxide suspension and 45.7 kg of a 32% by weight aqueous phosphoric acid solution were prepared such that the molar ratio Ca/P was 1.67. The liquids were simultaneously added dropwise to 112.5 kg of water heated to 98° C. over 1 hour, while controlling the pH of the reaction mixture to be maintained in the range of 8.5 to 9.5. After the completion of the dropwise addition, the reaction mixture was further aged with stirring for 30 minutes, and then filtered and water-washed.

Subsequently, the resulting product was subjected to tray drying under a temperature condition of 100° C. using a forced convection constant temperature oven (Yamato Scientific Co., Ltd.; DKN812), and subjected to dry grinding using a Comil (Powrex Corporation; QUADRO COMIL 194) and an ACM Pulverizer (Hosokawa Micron Corporation; 10A) to give a calcium phosphate powder. Analysis of the crystal structure by X-ray diffraction for the resulting calcium phosphate powder confirmed that the calcium phosphate powder was hydroxyapatite (HAP), as shown in FIG. 1.

Example 7

92.5 kg of a 20% by weight calcium hydroxide suspension and 45.7 kg of a 32% by weight aqueous phosphoric acid solution were prepared such that the molar ratio Ca/P was 1.67. The liquids were simultaneously added dropwise to 112.5 kg of water heated to 98° C. over 1 hour, while controlling the pH of the reaction mixture to be maintained in the range of 8.5 to 9.5. After the completion of the dropwise addition, the reaction mixture was further aged with stirring for 30 minutes, and then filtered and water-washed.

Figure 2:
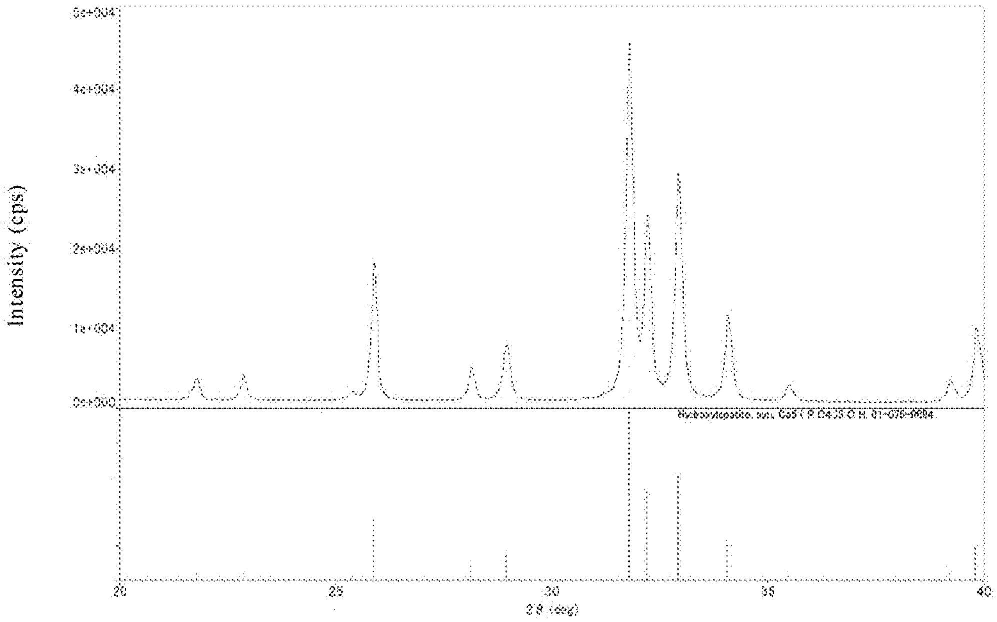
FIG. 2 shows the result of measuring the crystal structure for the calcium phosphate powder of Example 7.

Subsequently, the resulting product was suspended in water such that the calcium phosphate powder content was 10% by weight, and the suspension was subjected to wet grinding using a dyno-mill (Shinmaru Enterprises Corporation; Model MULTI LAB) under 20 rpm, a zirconia bead diameter of 1.0 mm, and a bead amount of 4.03 kg (loading: 80%). The resulting product was further subjected to tray drying under a temperature condition of 100° C. using a forced convection constant temperature oven (Yamato Scientific Co., Ltd.; DKN812), and subjected to dry grinding using a micro-pulverizer (Hosokawa Micron Corporation; AP-B) to give a calcium phosphate powder. Analysis of the crystal structure by X-ray diffraction for the resulting calcium phosphate powder confirmed that the calcium phosphate powder was hydroxyapatite (HAP), as shown in FIG. 2.

Example 8

90.0 kg of a 20% by weight calcium hydroxide suspension and 49.6 kg of a 32% by weight aqueous phosphoric acid solution were prepared such that the molar ratio Ca/P was 1.50. The liquids were simultaneously added dropwise to 111.5 kg of water heated to 98° C. over 1 hour, while controlling the pH of the reaction mixture to be maintained in the range of 3.5 to 4.5. After the completion of the dropwise addition, the reaction mixture was further aged with stirring for 30 minutes, and then filtered and water-washed.

Figure 3:
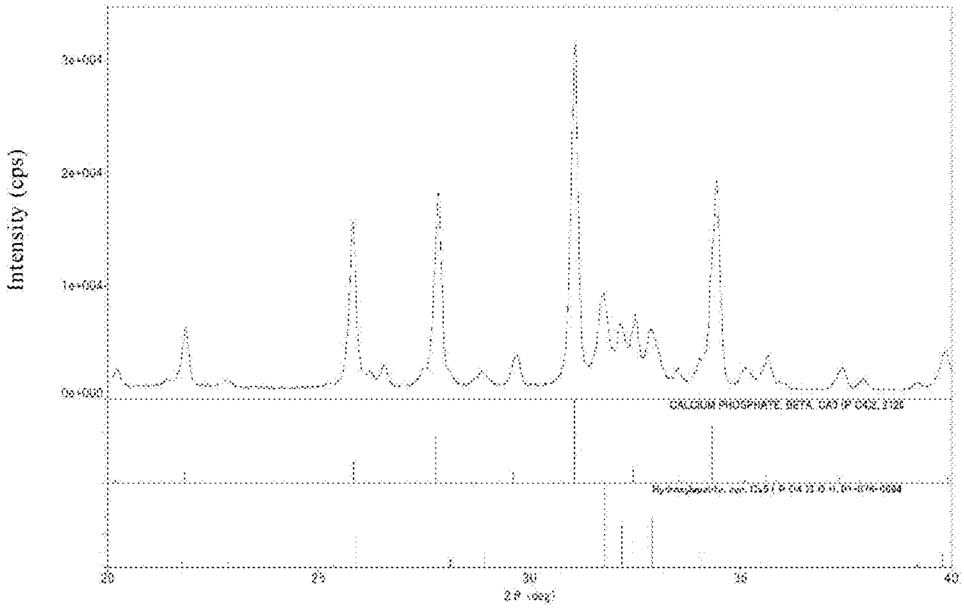
FIG. 3 shows the result of measuring the crystal structure for the calcium phosphate powder of Example 8.
Figure 7:
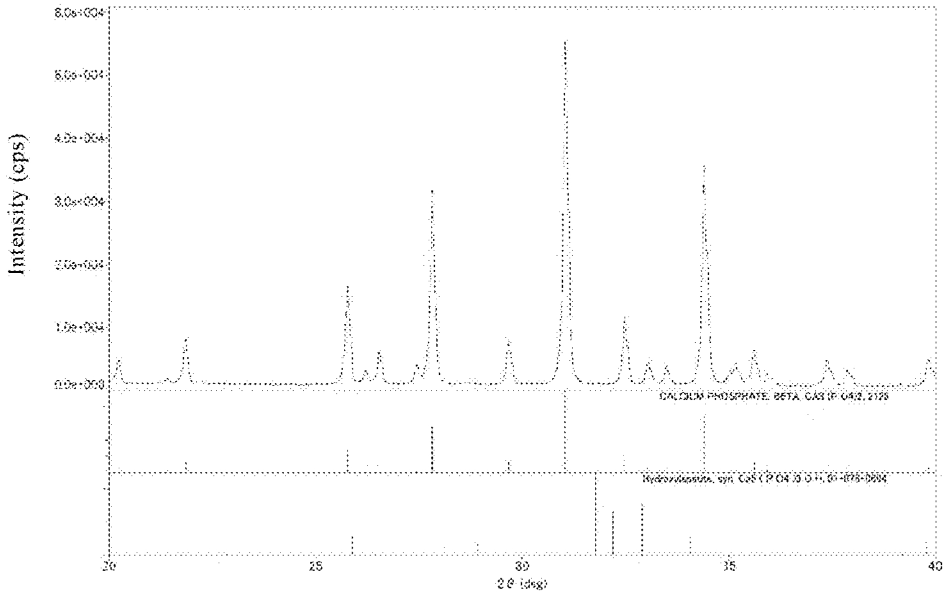
FIG. 7 shows the result of measuring the crystal structure for a three-dimensional additive manufacturing article obtained by subjecting a slurry for additive manufacturing containing the calcium phosphate powder of Example 8 to sintering treatment at 1100° C.

Subsequently, the resulting product was subjected to tray drying under a temperature condition of 100° C. using a forced convection constant temperature oven (Yamato Scientific Co., Ltd.; DKN812), and subjected to dry grinding using a Comil (Powrex Corporation; QUADRO COMIL 194) and a micro-pulverizer (Hosokawa Micron Corporation; AP-B). The resulting product was further fired at 650° C. for 3 hours (temperature increase rate: 100° C./h) using an electric furnace (Kitamura Denkiro Seisakusho K.K.; square-type electric furnace for oxidizing firing, model KSO-40, top cover winding-type). After allowing to cool, the resulting product was subjected to dry grinding using an ACM Pulverizer (Hosokawa Micron Corporation; 10A) to give a calcium phosphate powder. Analysis of the crystal structure by X-ray diffraction for the resulting calcium phosphate powder revealed a peak corresponding to hydroxyapatite (49% by weight) and a peak corresponding to β-TCP (51% by weight), as shown in FIG. 3. Furthermore, as described below, for a three-dimensional additive manufacturing article obtained by subjecting a slurry for additive manufacturing containing the resulting calcium phosphate powder to sintering treatment at 1100° C., analysis of the crystal structure by X-ray diffraction revealed only a peak of β-TCP, and did not reveal a peak of hydroxyapatite, as shown in FIG. 7. This shows that the peak of hydroxyapatite observed in FIG. 3 is the peak of calcium-deficient hydroxyapatite, which undergoes a structural change due to heat treatment. These analysis results confirmed that the calcium phosphate powder produced was a mixed crystal of 49% by weight of calcium-deficient hydroxyapatite and 51% by weight of β-TCP.

Example 9

90.0 kg of a 20% by weight calcium hydroxide suspension and 49.6 kg of a 32% by weight aqueous phosphoric acid solution were prepared such that the molar ratio Ca/P was 1.50. The liquids were simultaneously added dropwise to 111.5 kg of water heated to 98° C. over 1 hour, while controlling the pH of the reaction mixture to be maintained in the range of 3.5 to 4.5. After the completion of the dropwise addition, the reaction mixture was further aged with stirring for 30 minutes, and then filtered and water-washed.

Figure 4:
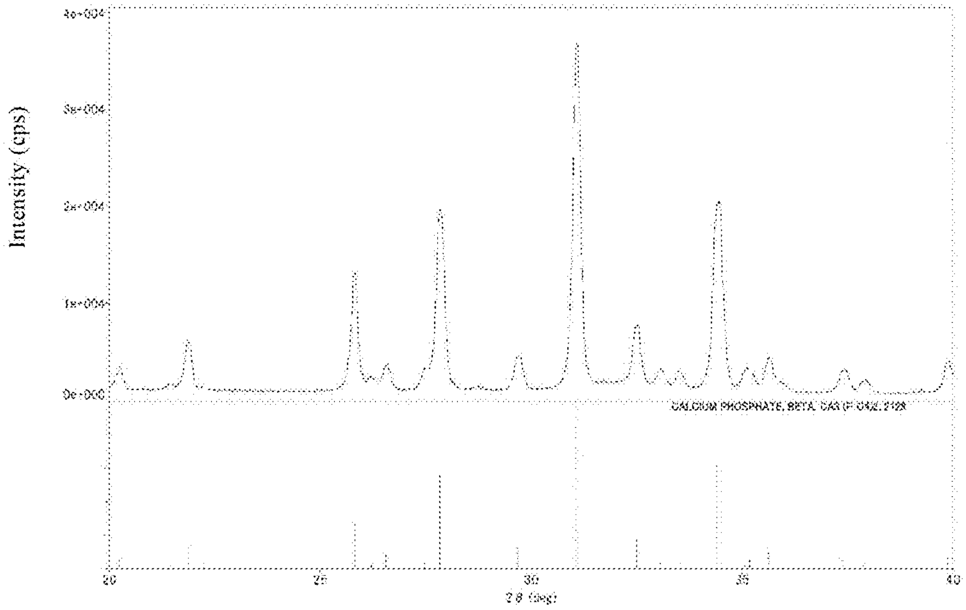
FIG. 4 shows the result of measuring the crystal structure for the calcium phosphate powder of Example 9.

Subsequently, the resulting product was subjected to tray drying under a temperature condition of 100° C. using a forced convection constant temperature oven (Yamato Scientific Co., Ltd.; DKN812), and subjected to dry grinding using a Comil (Powrex Corporation; QUADRO COMIL 194) and a micro-pulverizer (Hosokawa Micron Corporation; AP-B). The resulting product was further fired at 750° C. for 3 hours (temperature increase rate: 100° C./h) using an electric furnace (Kusaba Chemical Co., Ltd.; KY-5NX). After allowing to cool, the resulting product was suspended in water to 10% by weight, and the suspension was subjected to wet grinding using a dyno-mill (Shinmaru Enterprises Corporation; Model MULTI LAB) under 20 rpm, a zirconia bead diameter of 1.0 mm, and a bead amount of 4.03 kg (loading: 80%). The resulting product was further subjected to tray drying under a temperature condition of 100° C. using a forced convection constant temperature oven (Yamato Scientific Co., Ltd.; DKN812), and subjected to dry grinding using a micro-pulverizer (Hosokawa Micron Corporation; AP-B) to give calcium phosphate (β-TCP) particles. Analysis of the crystal structure by X-ray diffraction for the resulting calcium phosphate powder confirmed that, as shown in FIG. 4, the calcium phosphate powder was β-TCP, and the β-TCP content was 99% by weight.

Comparative Example 1

6 L of water and 1 kg of calcium oxide were placed in a reaction vessel and the hydration reaction was carried out, and then water was added to the suspension to adjust the total amount to 15 L. Then, the resulting suspension was heated to 50° C., and an aqueous phosphoric acid solution was added until pH 8 was reached. The resulting solution was aged by heating at 95° C. for 2 hours.

Then, the resulting reaction mixture was subjected to spray drying using a spray dryer with a disk-type spraying means, and the dried product was collected. The resulting dried product was further fired at 1150° C. for 3 hours (temperature increase rate: 65° C./h) using an electric furnace (Kusaba Chemical Co., Ltd.; KY-5NX). After allowing to cool, the resulting product was subjected to grinding using an ACM Pulverizer (Hosokawa Micron Corporation; 10A) to give calcium phosphate (HAP) particles.

Comparative Example 2

Commercial HAP particles (FUJIFILM Wako Pure Chemical Corporation; Apatite HAP, monoclinic) were used.

Comparative Example 3

Calcium phosphate (HAP) particles were obtained under the same conditions as in Example 3, except that the autoclave temperature was changed to 200° C.

Comparative Example 4

3514.1 g of an 8.4% by weight calcium hydroxide suspension and 464.5 g of a 50% by weight aqueous phosphoric acid solution were prepared such that the molar ratio Ca/P was 1.67. The phosphoric acid was added dropwise to the calcium hydroxide suspension at 20° C. while stirring at 300 rpm over 3 hours, and then the reaction mixture was further aged with stirring for 1 hour.

Subsequently, the resulting product was subjected to wet grinding using an Ultra Apex Mill (Kotobuki Industries Co., Ltd.; UAM-015) under 41.6 Hz, a pump speed of 2, a zirconia bead diameter of 0.3 mm, and a bead amount of 400 g (loading: 64%). Then, the resulting solution was subjected to hydrothermal treatment in an autoclave (Taiatsu Glass Kogyo K.K.; model TAS-09-20-300) at 280° C. for 3 hours.

The resulting product was further subjected to tray drying under a temperature condition of 100° C. using a forced convection constant temperature oven (Yamato Scientific Co., Ltd.; DKM400), and subjected to dry grinding using a micro-pulverizer (Hosokawa Micron Corporation; AP-B) to give calcium phosphate (HAP) particles.

Comparative Example 5

The HAP particles obtained in Comparative Example 3 were fired at 1000° C. for 3 hours (temperature increase rate: 100° C./h) using an electric furnace (Kusaba Chemical Co., Ltd.; KY-5NX), and subjected to dry grinding using a micro-pulverizer (Hosokawa Micron Corporation; AP-B) to give calcium phosphate (HAP) particles.

Comparative Example 6

1200.0 g of a 20% by weight calcium hydroxide suspension and 742.1 g of a 32% by weight aqueous phosphoric acid solution were prepared such that the molar ratio Ca/P was 1.67. Each of the liquids was preheated to 80° C., and the liquids were simultaneously added dropwise to 1785.0 mL of water heated to 98° C. while stirring at 300 rpm over 1 hour, while controlling the temperature to be maintained at 98° C. and the pH of the reaction mixture to be maintained in the range of 7.0 to 7.5. After the completion of the dropwise addition, the reaction mixture was further aged with stirring for 30 minutes. Then, the resulting product was subjected to tray drying under a temperature condition of 100° C. using a forced convection constant temperature oven (Yamato Scientific Co., Ltd.; DKM400) to give calcium phosphate (HAP) particles.

Comparative Example 7

1200.0 g of a 20% by weight calcium hydroxide suspension and 742.1 g of a 32% by weight aqueous phosphoric acid solution were prepared such that the molar ratio Ca/P was 1.67. Each of the liquids was preheated to 80° C., and the liquids were simultaneously added dropwise to 1785.0 mL of water heated to 98° C. while stirring at 300 rpm over 1 hour, while controlling the temperature to be maintained at 98° C. and the pH of the reaction mixture to be maintained in the range of 7.0 to 7.5. After the completion of the dropwise addition, the reaction mixture was further stirred for 30 minutes, and the precipitated crystals of hydroxyapatite were subjected to wet grinding using an Ultra Apex Mill (Kotobuki Industries Co., Ltd.; UAM-015) under 41.6 Hz, a pump speed of 2, a zirconia bead diameter of 0.3 mm, and a bead amount of 400 g (loading: 64%). Then, the resulting product was subjected to tray drying under a temperature condition of 100° C. using a forced convection constant temperature oven (Yamato Scientific Co., Ltd.; DKM400), and subjected to dry grinding using a micro-pulverizer (Hosokawa Micron Corporation; AP-B) to give calcium phosphate (HAP) particles.

1-2. Methods of Evaluating Physical Properties of Calcium Phosphate Powders

For each of the calcium phosphate powders produced, average particle size/particle size distribution/number average diameter, pore volume (gas adsorption method), BET specific surface area, average pore size (gas adsorption method), loose bulk density, packed bulk density, crystal structure, and content were evaluated, using the following methods.

[Average Particle Size/Particle Size Distribution/Number Average Diameter]

A suspension prepared by adding 0.4 g of the calcium phosphate powder and 0.02 g of a dispersing agent (product name "Celuna D-305" (manufactured by Chukyo Yushi Co., Ltd.)) to 5 g of water was dispersed in water. The particle size distribution was measured using a laser diffraction/scattering particle size distribution analyzer (MicrotracBEL Corp.; Microtrac MT3300EXII"), and $D_{10}$ (particle size when the cumulative percentage reaches 10%), $D_{50}$ (average particle size), $D_{90}$ (particle size when the cumulative percentage reaches 90%), and number average diameter (particle size when the cumulative percentage calculated in terms of number reaches 50%) were obtained.

[Pore Volume of Mesopores (2 to 50 nm) (Gas Adsorption Method)]

Using a high-speed specific surface area and pore distribution analyzer (Quantachrome Corporation; NOVA-4000), the pore volume of mesopores (2 to 50 nm) was obtained using the following method. First, 0.1 g or 1.0 g of the calcium phosphate powder was accurately weighed and sealed in a sorbent tube, and then degassed at 105° C. for 3 hours. Then, a nitrogen gas adsorption isotherm under a liquid nitrogen gas temperature was obtained, and the pore volume (cc/g) of mesopores (2 to 50 nm) was calculated using the BJH method.

[Pore Volume of Macropores (50 to 200 nm) (Gas Adsorption Method)]

Using a high-speed specific surface area and pore distribution analyzer (Quantachrome Corporation; NOVA-4000), the pore volume of macropores (50 to 200 nm) was obtained using the following method. First, 0.1 g or 1.0 g of the calcium phosphate powder was accurately weighed and sealed in a sorbent tube, and then degassed at 105° C. for 3 hours. Then, a nitrogen gas adsorption isotherm under a liquid nitrogen gas temperature was obtained, and the pore volume (cc/g) of macropores (50 to 200 nm) was calculated using the BJH method.

[BET Specific Surface Area]

Using a high-speed specific surface area and pore distribution analyzer (Quantachrome Corporation; NOVA-4000), the BET specific surface area was measured under the following operation conditions:

pretreatment: 0.1 g or 1.0 g of the calcium phosphate powder was accurately weighed and sealed in a sorbent tube, and then degassed at 105° C. for 3 hours.

measurement and analysis: a nitrogen gas adsorption isotherm under a liquid nitrogen gas temperature was obtained, and the specific surface area ($m^2/g$) was calculated according to the multi-point BET method, using the adsorption isotherm.

[Average Pore Size]

First, using a high-speed specific surface area and pore distribution analyzer (Quantachrome Corporation; NOVA-4000), the total pore volume was measured using the gas adsorption method, under the following operation conditions:

pretreatment: 0.1 g or 1.0 g of the calcium phosphate powder was accurately weighed and sealed in a sorbent tube, and then degassed at 105° C. for 3 hours.

measurement and analysis: a nitrogen gas adsorption isotherm under a liquid nitrogen gas temperature was obtained, and the total pore volume (cc/g) was calculated from the gas adsorption amount at a relative pressure P/P0 (P0: saturation vapor pressure) of 0.995.

Using the BET specific surface area and the total pore volume (gas adsorption method) obtained above, the average pore size (gas adsorption method) was calculated according to the following formula:

average pore size (nm)=4V/S×1000

V: total pore volume (gas adsorption method) (cc/g)

S: BET specific surface area ($m^2/g$)

[Loose Bulk Density]

Using a Powder Tester (Hosokawa Micron Corporation; PT-X), "loose bulk density" of the apparatus was selected, and the apparatus was operated using a cup capacity of 10 $cm^3$, a sieve with a mesh size of 710 μm, a vibration time of 50 seconds, and an amplitude of 0.5 mm, and falling of the calcium phosphate powder was stopped when the cup was filled with the powder to overflowing. The powder was leveled by removing the portion of the powder raised from the top of the cup, and the weight of the empty cup was subtracted from the weight of the cup containing the powder, and then the powder weight per $cm^3$ was obtained as the loose bulk density (g/mL).

[Packed Bulk Density (Tapped Density)]

After the measurement of the loose bulk density, a cylinder for tapped density measurement (inner diameter: 2.2 cm, height: 3.2 cm) was subsequently mounted to the top portion of the cup, as indicated on the apparatus. Then, the calcium phosphate powder was allowed to fall into the cylinder through the sieve with a mesh size of 710 μm that was being vibrated at an amplitude of 0.5 mm, until the cylinder was filled with the calcium phosphate powder to about 80% of the capacity of the cylinder. Tapping was started in this state, and tapping was performed a total of 180 times. During tapping, when the amount of the calcium phosphate powder in the cylinder was compacted to about 20% of the capacity of the cylinder, as indicated on the apparatus, the calcium phosphate powder was allowed to fall again into the cylinder through the sieve with a mesh size of 710 μm that was being vibrated at an amplitude of 0.5 mm, until the cylinder was refilled with the calcium phosphate powder to about 80% of the capacity of the cylinder. After the completion of the tapping, the cylinder was removed, the powder was leveled by removing the portion of the powder raised from the top of the cup, and the weight of the cup containing the powder was measured. From this weight, the weight of the empty cup was subtracted to calculate the powder weight in the cup, and the powder weight per $cm^3$ was obtained as the packed bulk density (g/mL).

[Crystal Structure]

Using an X-ray diffractometer (Rigaku Corporation; SmartLab), measurement was performed under the following conditions. The measurement conditions were as follows: tube: Cu, tube voltage: 40 kV, tube current: 30 mA, scan axis 2θ/0, scan mode: continuous, range specification: absolute, scan range: 2θ=20 to 40°, scan speed/counting time: 4.0°/min, step width: 0.02°, entrance slit: 2/3°, longitudinal limiting slit: 10 mm, receiving slit 1: 10 mm, receiving slit 2: 10 mm, detector: D/teX Ultra).

[Content]

From the measurement results of crystal structures obtained above, β-TCP and HAP contents were measured using the RIR (Reference Intensity Ratio) method of the integrated powder X-ray analysis software PDXL2. At that time, the DB card number 2128 was used for β-TCP, and the DB card number 01-076-0694 was used for HAP.

2. Production and Evaluation of Additive Manufacturing Slurries 2-1. Production of Additive Manufacturing Slurries 20.0 g of each calcium phosphate powder was accurately measured and placed in a container for a stirring and defoaming apparatus. Then, a mixture of an ultraviolet curable resin and a dispersing agent was gradually added, and the mixture was stirred in the stirring and defoaming apparatus. For the calcium phosphate particles of Examples 1 to 5, 7 and 9, and Comparative Examples 1 to 7, a mixture of an ultraviolet curable resin (SK Fine Co., Ltd.; an acrylic photocurable resin for the SZ series) and a dispersing agent (SK Fine Co., Ltd.; a polycarboxylic acid-based dispersing agent) was used. For the calcium phosphate particles of Examples 6 and 8, a mixture of an ultraviolet curable resin (SK Fine Co., Ltd.; an acrylic photocurable resin for the SZ series) and dispersing agents (SK Fine Co., Ltd.; a polycarboxylic acid-based dispersing agent and a fatty acid amide-based dispersing agent) was used. The addition of the mixture was stopped at the point when flowability was observed, thus giving a slurry for additive manufacturing. As used herein, the "point when flowability was observed" refers to the point when the slurry was formed by the addition of the mixture, and the point when no agglomeration of the calcium phosphate powder due to the addition of the mixture was observed.

The concentration (% by weight) of the calcium phosphate powder in the slurry for additive manufacturing was obtained from the ratio of the weight of the calcium phosphate powder to the weight of the slurry for additive manufacturing. The concentration (% by volume) of the calcium phosphate powder in the slurry for additive manufacturing was obtained from the volume of the calcium phosphate powder to the volume of the slurry for additive manufacturing (weight (g) of the calcium phosphate powder/true density (3.2 g/cm$^3$) of the HAP powder or true density (3.1 g/cm$^3$) of the β-TCP powder).

2-2. Methods of Evaluating Physical Properties of Additive Manufacturing Slurries 10 to 14 mL of the slurry for additive manufacturing obtained above was aliquoted into a 15 mL centrifuge tube A, and allowed to stand still for 3 days. After allowing to stand still, the liquid separated in the centrifuge tube A was transferred into another 15 mL centrifuge tube B, and the liquid amount at that time was defined as the separated liquid amount X. Furthermore, the centrifuge tube A was tilted at 45° and set such that the liquid falling from the centrifuge tube A without thixotropic properties entered the centrifuge tube B in which the separated liquid was collected, and allowed to stand still for 2 hours. After allowing to stand still for 2 hours, it was confirmed that the liquid no longer fell, and the liquid remaining in the centrifuge tube A and in which agglomeration of the powder was observed was defined as the sedimented liquid amount Y. After this operation, because of settling of solids, flowability was lost in the liquid remaining in the centrifuge tube A and in which agglomeration of the powder was observed. Thus, if this liquid is used in additive manufacturing, it may be separated in the manufacturing apparatus, possibly leading to non-uniformity in manufacturing concentration and clogging of the apparatus. From the values of the separated liquid amount X and the sedimented liquid amount Y, the separation ratio and the sedimentation ratio were obtained according to the following formulae:

$$\text{Separation ratio (\%)}=\{\text{separated liquid amount } X \text{ (mL)/amount (mL) of the slurry for additive manufacturing placed in the centrifuge tube } A \text{ at the beginning of the test}\}\times 100$$

$$\text{Sedimentation ratio (\%)}=\{\text{sedimented liquid amount } Y \text{ (mL)/amount (mL) of the slurry for additive manufacturing placed in the centrifuge tube } A \text{ at the beginning of the test}\}\times 100 \quad \text{[Expression 1]}$$

3. Production and Evaluation of Three-Dimensional Additive Manufacturing Articles 3-1. Production of Three-Dimensional Additive Manufacturing Articles Using each slurry for additive manufacturing obtained as in "2-1. Production of Additive Manufacturing Slurries" above, stereolithography was performed with a stereolithography apparatus (SHASHIN KAGAKU CO., LTD.; high-resolution stereolithography apparatus for ceramics of the SZ series) such that the resulting three-dimensional additive manufacturing article would have a cylindrical shape with a diameter of 5 mm and a height of 12.5 mm, thus giving a three-dimensional layered cured product. Then, after uncured resin was removed with ethanol, the three-dimensional layered cured product was subjected to degreasing treatment and sintering treatment using a hot-temperature electric furnace (Advantec Toyo Kaisha, Ltd.; FUH732PA) under the following conditions to give a three-dimensional additive manufacturing article. In the case of the three-dimensional layered cured products formed using the additive manufacturing slurries containing the calcium phosphate powders of Examples 1 to 5 and Comparative Examples 1 to 7, each three-dimensional layered cured product was subjected to degreasing treatment by increasing the temperature to 600° C. at a temperature increase time (30° C./h), followed by sintering treatment by increasing the temperature to 1300° C. at a temperature increase rate of 100° C./h and maintaining the temperature of 1300° C. for 3 hours, thus giving a three-dimensional additive manufacturing article. In the case of the three-dimensional layered cured product formed using the a slurry for additive manufacturing containing the calcium phosphate powder of Example 6, the three-dimensional layered cured product was subjected to degreasing treatment by increasing the temperature to 500° C. at a temperature increase time (30° C./h) and maintaining the temperature of 500° C. for 6 hours, followed by sintering treatment by increasing the temperature at a temperature increase rate of 100° C./h to 1000° C., 1100° C., or 1300° C., and maintaining each increased temperature for 3 hours, thus giving three-dimensional additive manufacturing articles at the different sintering treatment temperatures. In the case of the three-dimensional layered cured product formed using the slurry for additive manufacturing containing the calcium phosphate powder of Example 8, three-dimensional additive manufacturing articles were obtained under the same conditions as used for Example 6, except that the temperature was increased to 1000° C. or 1100° C.

3-2. Methods of Evaluating Physical Properties of Three-Dimensional Additive Manufacturing Articles, and Production Suitability of Three-Dimensional Additive Manufacturing Articles Manufacturability, warping/deformation/breakability, compressive strength, appearance, and crystal structure were evaluated using the following methods.

[Manufacturability]

Manufacturability was evaluated based on the following criteria:

A: Additive manufacturing could be performed to 10 mm or more.

B: Additive manufacturing could not be performed to 10 mm or more.

C: The slurry for additive manufacturing could be spread on the layering table of the manufacturing apparatus; however, because of unevenness formed on the coating surface, a layer was not formed thereon, and manufacturing could not be performed.

D: Because of sedimentation of solids in the slurry, the slurry for additive manufacturing could not be spread on the layering table of the manufacturing apparatus, and manufacturing could not be performed.

[Warping/Deformation/Breakability]

The appearance of each three-dimensional additive manufacturing article was visually observed, and warping, deformation, and breakability were evaluated based on the following criteria:

A: The three-dimensional additive manufacturing article was free from warping, deformation, and breakage, as compared with the three-dimensional layered cured product from which uncured resin was removed.

B: The three-dimensional additive manufacturing article showed only warping or deformation, as compared with the three-dimensional layered cured product from which uncured resin was removed.

C: The three-dimensional additive manufacturing article showed only breakage, as compared with the three-dimensional layered cured product from which uncured resin was removed.

D: The three-dimensional additive manufacturing article showed warping, deformation, and breakage, as compared with the three-dimensional layered cured product from which uncured resin was removed.

[Compressive Strength]

The compressive strength of each three-dimensional additive manufacturing article was measured using a precision universal material testing machine (Instron Japan; Model 4507). Specifically, the compressive strength of the three-dimensional additive manufacturing article was measured by compressing the three-dimensional additive manufacturing article in the direction vertical to its layered surface (bottom surface), under a 5 kN load cell, an indenter with a diameter of 50 mm, and a test speed of 0.5 mm/min, according to JIS R1608 (2003).

[Appearance]

The appearance of each three-dimensional additive manufacturing article was observed with a field emission scanning electron microscope (Hitachi High-Technologies Corporation; SU-8220) at 100 times and 1000 times.

[Crystal Structure]

Using an X-ray diffractometer (Rigaku Corporation; SmartLab), measurement was performed under the following conditions. The measurement conditions were as follows: tube: Cu, tube voltage: 40 kV, tube current: 30 mA, scan axis 2θ/0, scan mode: continuous, range specification: absolute, scan range: 2θ=20 to 40°, scan speed/counting time: 4.0°/min, step width: 0.02°, entrance slit: 2/3°, longitudinal limiting slit: 10 mm, receiving slit 1: 10 mm, receiving slit 2: 10 mm, detector: D/teX Ultra).

4. Results

Figure 5:
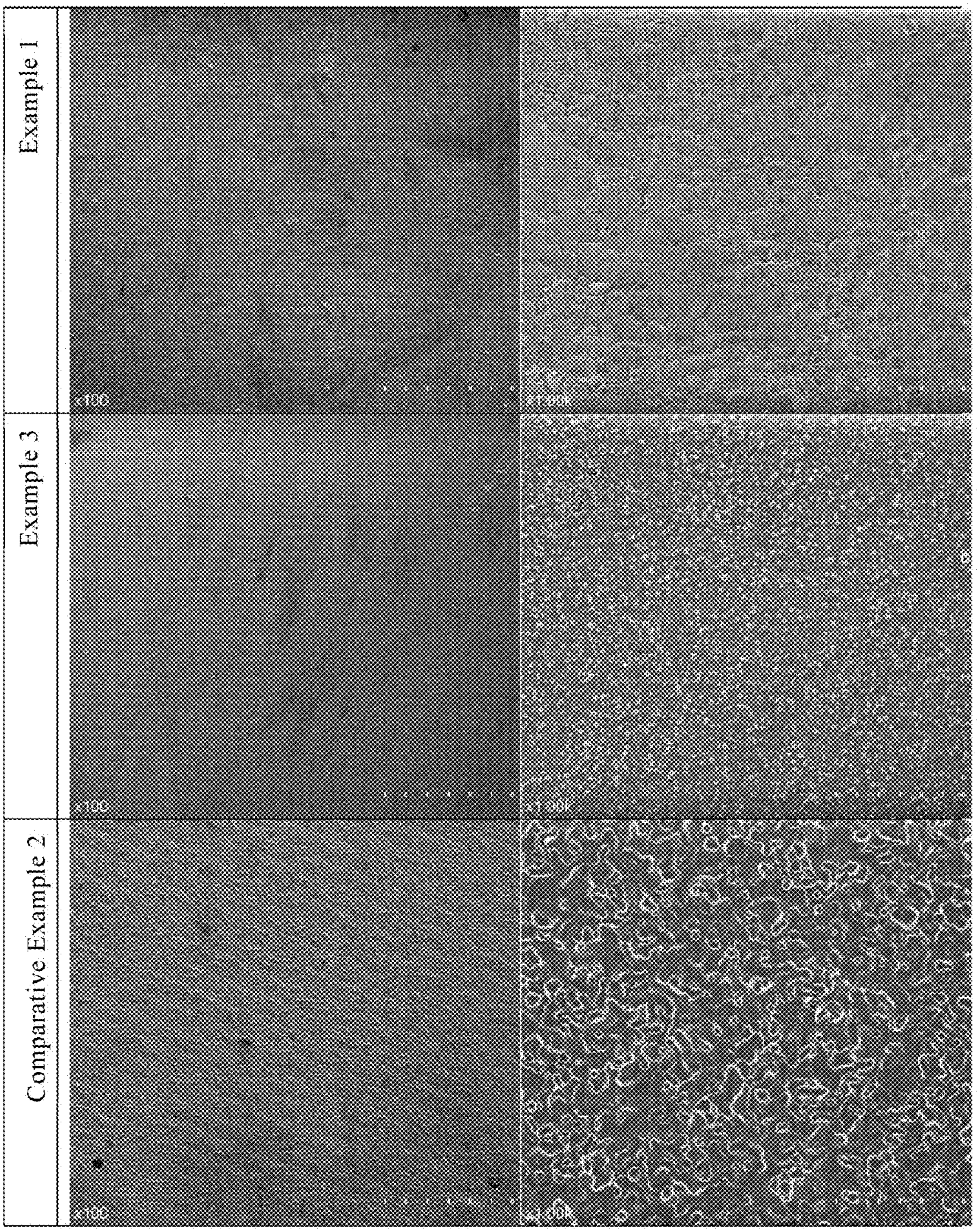
FIG. 5 shows images of the surfaces of three-dimensional additive manufacturing articles produced using the calcium phosphate powders of Examples 1 and 3, and Comparative Example 2 observed with a field emission scanning electron microscope.
Figure 6:
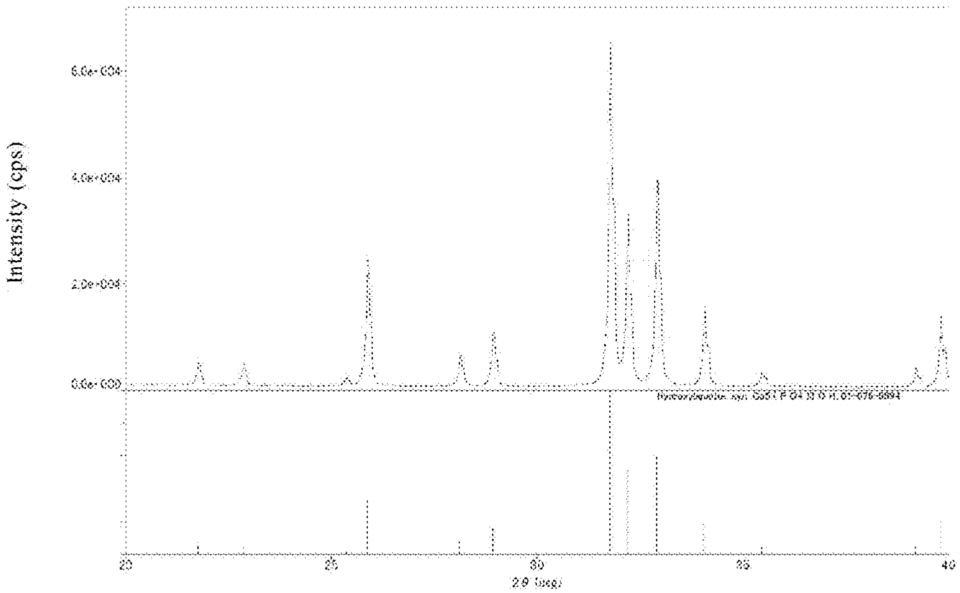
FIG. 6 shows the result of measuring the crystal structure for a three-dimensional additive manufacturing article obtained by subjecting a slurry for additive manufacturing containing the calcium phosphate powder of Example 6 to sintering treatment at 1100° C.

The results obtained are shown in Tables 1 to 4 and FIGS. 1 to 7. FIG. 1 shows the result of measuring the crystal structure of the calcium phosphate powder of Example 6; FIG. 2 shows the result of measuring the crystal structure of the calcium phosphate powder of Example 7; FIG. 3 shows the result of measuring the crystal structure of the calcium phosphate powder of Example 8; and FIG. 4 shows the result of measuring the crystal structure of the calcium phosphate powder of Example 9. FIG. 5 shows images of the surfaces of three-dimensional additive manufacturing articles produced using the calcium phosphate powders of Examples 1 and 3, and Comparative Example 2 observed with a field emission scanning electron microscope. FIG. 6 shows the result of measuring the crystal structure of a three-dimensional additive manufacturing article obtained by subjecting a slurry for additive manufacturing containing the calcium phosphate powder of Example 6 to sintering treatment at 1100° C. FIG. 7 shows the result of measuring the crystal structure of a three-dimensional additive manufacturing article obtained by subjecting a slurry for additive manufacturing containing the calcium phosphate powder of Example 8 to sintering treatment at 1100° C.

The calcium phosphate powders of Examples 1 to 9, having an average particle size of 0.1 to 5.0 μm, and having a pore volume of mesopores (pore size: 2 to 50 nm) of 0.01 to 0.06 cc/g, enabled the production of additive manufacturing slurries with excellent dispersion stability, in which the calcium phosphate powders did not separate from the ultraviolet curable resin even after being allowed to stand for a long time.

Moreover, by performing stereolithography using the additive manufacturing slurries containing the calcium phosphate powders of Examples 1 to 5, it was possible to create three-dimensional additive manufacturing articles with high strength, which did not break during degreasing and sintering, and had a compressive strength of 84 to 195 MPa. Moreover, by performing stereolithography using the slurry for additive manufacturing containing the calcium phosphate powder of Example 6, it was possible to create a three-dimensional additive manufacturing article with high strength, which did not break even when the temperature for degreasing and sintering was varied, and had a compressive strength of about 51 to 113 MPa. Furthermore, the three-dimensional additive manufacturing article obtained using the calcium phosphate powder of Example 8 was also created as a three-dimensional additive manufacturing article with high strength, which did not break even when the temperature for degreasing and sintering was varied, and had a compressive strength of about 78 to 221 MPa even though the calcium phosphate powder was β-TCP, which is generally considered to be inferior in strength to HAP. These results show that, by using the calcium phosphate powder of the present invention, it is possible to produce an artificial bone with high strength suitable for a desired site, because the strength of the three-dimensional additive manufacturing article can be varied as desired in a high-strength range.

On the other hand, the calcium phosphate powders of Comparative Examples 1 and 5, having a pore volume of mesopores (pore size: 2 to 50 nm) as small as less than 0.01 cc/g, had poor dispersibility during the production of additive manufacturing slurries, and showed sedimentation. The calcium phosphate powders of Comparative Examples 2 and 6, which had a satisfactory pore volume of mesopores, but had an average particle size as large as above 5.0 μm, had a small pore volume per particle; therefore, the additive manufacturing slurries did not have the required thixotropic properties, and also had low dispersion stability. Thus, because of unevenness formed on the coating surface, a layer was not formed thereon, and manufacturing could not be performed, or additive manufacturing could not be performed to 10 mm or more. Moreover, the calcium phosphate powders of Comparative Examples 3, 4 and 7, having a pore volume of mesopores as large as above 0.06 cc/g, resulted in a high content of the photocurable resin in the additive manufacturing slurries; therefore, when these slurries were subjected to stereolithography, the manufacturing articles after degreasing and sintering underwent a large amount of shrinkage, leading to warping, deformation, breakage, or insufficient strength of the three-dimensional additive manufacturing articles.

Furthermore, as shown in FIG. 5, the three-dimensional additive manufacturing articles (stereolithographic articles) produced using the calcium phosphate powders of Examples 1 and 3 had less irregularities on the surfaces of the three-dimensional additive manufacturing articles, and smoother, as compared with Comparative Example 2. That is, this result shows that, by using the calcium phosphate powder of the present invention, it is possible to produce a three-dimensional additive manufacturing article with high accuracy, having a flat surface with no surface irregularities from a microscopic viewpoint.

As shown in FIG. 6, it can be seen that the calcium phosphate powder of Example 6 maintains the crystal structure of hydroxyapatite even in the three-dimensional additive manufacturing article.

Moreover, as shown in FIG. 7, the three-dimensional additive manufacturing article obtained using the calcium phosphate powder of Example 8 was a single crystal of β-TCP; however, as shown in FIG. 3, X-ray diffraction of the calcium phosphate powder of Example 8 revealed a peak corresponding to hydroxyapatite and a peak corresponding to β-TCP. That is, it is observed that the peak corresponding to hydroxyapatite in FIG. 3 is the peak of calcium-deficient hydroxyapatite, which undergoes a structural change due to heat treatment, and the calcium phosphate powder of Example 8 is a mixed crystal containing the crystal structures of calcium-deficient hydroxyapatite and β-TCP.

TABLE 1

| | | | Ex. 1 | Ex. 2 | Ex. 3 | Ex. 4 | Ex. 5 |
|---|---|---|---|---|---|---|---|
| Evaluation of Physical Properties of Calcium Phosphate Powder | D10 (μm) | | 0.33 | 0.35 | 0.21 | 0.73 | 0.38 |
| | D50 (Average Particle Size) (μm) | | 0.64 | 0.81 | 0.46 | 2.88 | 0.94 |
| | D90 (μm) | | 2.47 | 3.28 | 2.93 | 16.96 | 4.37 |
| | Number Average Diameter (μm) | | 0.35 | 0.35 | 0.20 | 0.59 | 0.37 |
| | Pore Volume (Gas Adsorption Method) (cc/g) | Mesopores | 0.025 | 0.042 | 0.044 | 0.022 | 0.030 |
| | | Macropores | 0.040 | 0.075 | 0.033 | 0.029 | 0.032 |
| | BET Specific Surface Area ($m^2/g$) | | 8.7 | 15.2 | 17.3 | 12.0 | 14.4 |
| | Average Pore Size (nm) | | 30.6 | 31.3 | 17.3 | 17.6 | 17.6 |
| | Loose Bulk Density (g/mL) | | 0.26 | 0.30 | 0.18 | 0.24 | 0.30 |
| | Packed Bulk Density (g/mL) | | 0.62 | 0.72 | 0.48 | 0.57 | 0.69 |
| Evaluation of Physical Properties of Slurry for Additive Manufacturing | Calcium Phosphate Concentration (% by volume) in Slurry | | 57 | 52 | 45 | 52 | 57 |
| | Calcium Phosphate Concentration (% by weight) in Slurry | | 79 | 76 | 70 | 76 | 79 |
| | Separation Ratio (%) | | 0 | 0 | 0 | 0 | 0 |
| | Sedimentation Ratio (%) | | 0 | 0 | 0 | 0 | 0 |
| Evaluation of Physical Properties of Three-Dimensional Additive Manufacturing Article | Manufacturability | | A | A | A | A | A |
| | Warping/Deformation/Breakability | | A | A | A | A | A |
| | Compressive Strength (MPa) | | 181.9 | 84.0 | 194.8 | — | 114.5 |

In the table, "—" indicates not measured.

TABLE 2

| | | | Ex. 6 | Ex. 7 | Ex. 8 | Ex. 9 |
|---|---|---|---|---|---|---|
| Evaluation of Physical Properties of Calcium Phosphate Powder | D10 (μm) | | 2.13 | 0.44 | 1.56 | 0.49 |
| | D50 (Average Particle Size) (μm) | | 3.87 | 1.21 | 4.74 | 1.05 |
| | D90 (μm) | | 6.62 | 3.10 | 10.30 | 2.42 |
| | Number Average Diameter (μm) | | 1.94 | 0.45 | 0.77 | 0.53 |
| | Pore Volume (Gas Adsorption Method) (cc/g) | Mesopores | 0.024 | 0.051 | 0.031 | 0.042 |
| | | Macropores | 0.026 | 0.047 | 0.023 | 0.044 |
| | BET Specific Surface Area ($m^2/g$) | | 9.2 | 19.7 | 12.4 | 14.6 |
| | Average Pore Size (nm) | | 21.6 | 19.7 | 17.0 | 23.8 |
| | Loose Bulk Density (g/mL) | | 0.27 | 0.27 | 0.25 | 0.30 |
| | Packed Bulk Density (g/mL) | | 0.65 | 0.62 | 0.57 | 0.65 |
| Evaluation of Physical Properties of Slurry for Additive Manufacturing | Calcium Phosphate Concentration (% by volume) in Slurry | | 41 | 47 | 47 | 50 |
| | Calcium Phosphate Concentration (% by weight) in Slurry | | 67 | 72 | 71 | 74 |
| | Separation Ratio (%) | | 0 | — | 0 | — |
| | Sedimentation Ratio (%) | | 0 | — | 0 | — |
| Degreasing Treatment and Sintering/Firing Treatment of Three-Dimensional Additive Manufacturing Article | Temperature (° C.) of Degreasing Treatment | | 500 500 | — | 500 500 | — |
| | Temperature (° C.) of Sintering/Firing Treatment | | 1100 1300 | — | 1000 1100 | — |
| Evaluation of Physical Properties of Three-Dimensional Additive Manufacturing Article | Manufacturability | | A A | — | A A | — |
| | Warping/Deformation/Breakability | | A A | — | A A | — |
| | Compressive Strength (MPa) | | 51.6 113.2 | — | 78.3 221.3 | — |

In the table, "—" indicates not measured.

TABLE 3

| | | | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|
| Evaluation of Physical Properties of Calcium Phosphate Powder | D10 (μm) | | 0.88 | 3.10 | 0.25 | 1.89 | 0.59 | 12.27 | 0.52 |
| | D50 (Average Particle Size) (μm) | | 2.29 | 6.15 | 0.61 | 4.50 | 3.37 | 19.71 | 2.13 |
| | D90 (μm) | | 8.45 | 11.87 | 3.95 | 12.57 | 15.68 | 30.57 | 12.94 |
| | Number Average Diameter (μm) | | 0.77 | 3.23 | 0.23 | 1.03 | 0.43 | 12.88 | 0.44 |
| | Pore Volume (Gas Adsorption Method) (cc/g) | Mesopores | 0.007 | 0.031 | 0.071 | 0.152 | 0.008 | 0.024 | 0.071 |
| | | Macropores | 0.005 | 0.021 | 0.113 | 0.236 | 0.005 | 0.016 | 0.119 |
| | BET Specific Surface Area ($m^2/g$) | | 3.6 | 10.2 | 23.2 | 42.3 | 2.1 | 6.5 | 26.0 |
| | Average Pore Size (nm) | | 13.4 | 19.4 | 31.6 | 36.5 | 38.7 | 23.1 | 29.0 |
| | Loose Bulk Density (g/mL) | | 0.48 | 0.19 | 0.18 | 0.18 | 0.29 | 0.40 | 0.37 |
| | Packed Bulk Density (g/mL) | | 1.14 | 0.52 | 0.47 | 0.45 | 0.70 | 0.62 | 0.81 |

TABLE 3-continued

| | | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| Evaluation of Physical Properties of Slurry for Additive Manufacturing | Calcium Phosphate Concentration (% by volume) in Slurry | 58 | 30 | 28 | 30 | 45 | 30 | 40 |
| | Calcium Phosphate Concentration (% by weight) in Slurry | 76 | 56 | 53 | 56 | 70 | 56 | 66 |
| | Separation Ratio (%) | 0 | 0 | 0 | 0 | 0 | 7 | 0 |
| | Sedimentation Ratio (%) | 24 | 19 | 0 | 0 | 18 | 87 | 0 |
| Evaluation of Physical Properties of Three-Dimensional Additive Manufacturing Article | Manufacturability | C | B | A | A | C | D | A |
| | Warping/Deformation/Breakability | — | B | D | D | — | — | A |
| | Compressive Strength (MPa) | — | — | — | — | — | — | 38.0 |

In the table, "—" indicates not measured.

The invention claimed is:

1. A method for producing a three-dimensional additive manufacturing article, comprising the following steps (1) to (4):

(1) forming a slurry layer using the slurry for additive manufacturing, the slurry comprising a calcium phosphate powder, wherein the calcium phosphate powder has:

(i) having an average particle size ($D_{50}$) of 0.1 to 5.0 μm, (ii) a $D_{10}$ of 1.0 μm or less, and (iii) a pore volume of mesopores (pore size: 2 to 50 nm) of 0.01 to 0.06 cc/g as measured by a gas adsorption method;

(2) curing the slurry layer by irradiation of laser light in a predetermined pattern shape;

(3) repeating steps (1) and (2) to form a three-dimensional layered cured product; and (4) removing uncured resin and cured resin from the three-dimensional layered cured product.

2. The method for producing a three-dimensional additive manufacturing article according to claim 1, wherein the three-dimensional additive manufacturing article is an implant.

3. The method for producing a three-dimensional additive manufacturing article according to claim 1, wherein the calcium phosphate contains at least one of hydroxyapatite, tricalcium phosphate, α-TCP, calcium-deficient hydroxyapatite, and β-TCP.

4. The method for producing a three-dimensional additive manufacturing article according to claim 1, wherein the calcium phosphate powder has a BET specific surface area of 0.1 to 20 $m^2/g$.

5. The method for producing a three-dimensional additive manufacturing article according to claim 1, wherein the calcium phosphate powder has a pore volume of macropores (pore size: 50 to 200 nm) of 0.02 to 0.10 cc/g as measured by the gas adsorption method.

* * * * *